US009504858B2

(12) United States Patent
Yuan et al.

(10) Patent No.: US 9,504,858 B2
(45) Date of Patent: *Nov. 29, 2016

(54) ZINC AMINO ACID HALIDE COMPLEX WITH CYSTEINE

(71) Applicant: Colgate-Palmolive Company, Piscataway, NJ (US)

(72) Inventors: Shaotang Yuan, East Brunswick, NJ (US); Long Pan, Cherry Hill, NJ (US); Laurence D. Du-Thumm, Princeton, NJ (US)

(73) Assignee: Colgate-Palmolive Company, New York, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/650,907

(22) PCT Filed: Nov. 7, 2013

(86) PCT No.: PCT/US2013/068852
§ 371 (c)(1),
(2) Date: Jun. 10, 2015

(87) PCT Pub. No.: WO2014/099164
PCT Pub. Date: Jun. 26, 2014

(65) Prior Publication Data
US 2015/0306008 A1    Oct. 29, 2015

Related U.S. Application Data

(63) Continuation-in-part of application No. PCT/US2013/046268, filed on Jun. 18, 2013, and a continuation-in-part of application No. PCT/US2012/070489, filed on Dec. 19, 2012, and a continuation-in-part of application No. PCT/US2012/070492, filed on Dec. 19, 2012, and a continuation-in-part of application No. PCT/US2012/070498, filed on Dec. 19, 2012, and a continuation-in-part of application No. PCT/US2012/070525, filed on Dec. 19, 2012, and a continuation-in-part of application No. PCT/US2012/070537, filed on Dec. 19, 2012, and a continuation-in-part of application No. PCT/US2012/070506, filed on Dec. 19, 2012, and a continuation-in-part of application No. PCT/US2012/070513, filed on Dec. 19, 2012, and a continuation-in-part of application No. PCT/US2012/070505, filed on Dec. 19, 2012, and a continuation-in-part of application No. PCT/US2012/070501, filed on Dec. 19, 2012, and a continuation-in-part of application No. PCT/US2012/070521, filed on Dec. 19, 2012, and a continuation-in-part of application No. PCT/US2012/070534, filed on Dec. 19, 2012, and a continuation-in-part of application No. PCT/US2013/050845, filed on Jul. 17, 2013.

(51) Int. Cl.
A61K 8/58      (2006.01)
A61K 8/46      (2006.01)
A61Q 11/00     (2006.01)
A61Q 15/00     (2006.01)
A61Q 19/10     (2006.01)
A61K 8/27      (2006.01)
A61K 8/44      (2006.01)
A61K 31/198    (2006.01)
A61K 31/555    (2006.01)
A61K 33/16     (2006.01)
A61K 33/30     (2006.01)

(52) U.S. Cl.
CPC .............. A61Q 11/00 (2013.01); A61K 8/27 (2013.01); A61K 8/44 (2013.01); A61K 8/447 (2013.01); A61K 31/198 (2013.01); A61K 31/555 (2013.01); A61K 33/16 (2013.01); A61K 33/30 (2013.01); A61Q 15/00 (2013.01); A61K 2800/58 (2013.01); A61Q 19/10 (2013.01)

(58) Field of Classification Search
USPC .................................. 424/641, 643; 556/118
See application file for complete search history.

(56) References Cited

U.S. PATENT DOCUMENTS

| 2,503,280 A | 4/1950  | Lockwood  |
| 2,507,088 A | 5/1950  | Bradley   |
| 2,527,686 A | 10/1950 | Sandberg  |
| 2,893,918 A | 7/1959  | Abramson  |
| 3,260,744 A | 7/1966  | Kenkichi  |
| 3,320,174 A | 5/1967  | Rubinfeld |

(Continued)

FOREIGN PATENT DOCUMENTS

| CN | 101606639 | 12/2009 |
| CN | 102811698 | 12/2012 |

(Continued)

OTHER PUBLICATIONS

Anonymous, "Zinc Lauryl Ether Sulphate, A New Approach to Skincare," Apr. 2004, Retrieved from Internet, http://www.erwebhosting.it/zsi/repository/Zinc%20Lauryl%20Ether%20Sulphate,%20A%20new%20approach%20to%20skin%20care.pdf, Retrieved Sep. 26, 2013.

(Continued)

Primary Examiner — Walter Webb

(57) ABSTRACT

Provided are compositions, e.g., oral and personal care products, comprising (i) a zinc amino acid halide complex, and (ii) cysteine in free or in orally or cosmetically acceptable salt form, together with methods of making and using the same.

17 Claims, No Drawings

(56) References Cited

U.S. PATENT DOCUMENTS

| | | |
|---|---|---|
| 3,372,188 A | 3/1968 | Terence |
| 3,535,421 A | 10/1970 | Briner |
| 3,538,230 A | 11/1970 | Morton |
| 3,678,154 A | 7/1972 | Briner |
| 3,741,911 A | 6/1973 | Shane |
| 3,862,307 A | 1/1975 | Di Giulio |
| 3,937,807 A | 2/1976 | Haefele |
| 3,941,818 A | 3/1976 | Abdel-Monem |
| 3,959,458 A | 5/1976 | Agricola et al. |
| 4,051,234 A | 9/1977 | Gieske et al. |
| 4,316,824 A | 2/1982 | Pancheri |
| 4,339,432 A | 7/1982 | Ritchey et al. |
| 4,340,583 A | 7/1982 | Wason |
| 4,487,757 A | 12/1984 | Kiozpeoplou |
| 4,565,693 A | 1/1986 | Marschner |
| 4,599,152 A | 7/1986 | Ashmead |
| 4,684,528 A | 8/1987 | Godfrey |
| 4,687,663 A | 8/1987 | Schaeffer |
| 4,842,847 A | 6/1989 | Amjad |
| 4,866,161 A | 9/1989 | Sikes et al. |
| 4,885,155 A | 12/1989 | Parran, Jr. et al. |
| 5,004,597 A | 4/1991 | Majeti et al. |
| 5,061,815 A | 10/1991 | Leu |
| 5,156,845 A | 10/1992 | Grodberg |
| 5,188,821 A | 2/1993 | Gaffar et al. |
| 5,192,531 A | 3/1993 | Gaffar et al. |
| 5,504,055 A | 4/1996 | Hsu |
| 5,643,559 A | 7/1997 | Eigen et al. |
| 5,698,724 A | 12/1997 | Anderson et al. |
| 5,707,679 A | 1/1998 | Nelson |
| 5,714,447 A | 2/1998 | Jones et al. |
| 5,911,978 A | 6/1999 | Carr et al. |
| 5,993,784 A | 11/1999 | Hill |
| 6,121,315 A | 9/2000 | Nair et al. |
| 6,156,293 A | 12/2000 | Jutila et al. |
| 6,607,711 B2 | 8/2003 | Pedersen |
| 6,685,920 B2 | 2/2004 | Baig et al. |
| 6,969,510 B2 | 11/2005 | Holerca et al. |
| 8,067,627 B2 | 11/2011 | Newsome et al. |
| 8,247,398 B2 | 8/2012 | Goel |
| 8,685,951 B2 * | 4/2014 | Basnakian ............ C07C 323/25 514/181 |
| 2004/0033916 A1 | 2/2004 | Kuzmin et al. |
| 2004/0042978 A1 | 3/2004 | Embro |
| 2004/0122088 A1 | 6/2004 | Newsome et al. |
| 2004/0198998 A1 | 10/2004 | Holerca et al. |
| 2006/0024252 A1 | 2/2006 | Esposito et al. |
| 2007/0071698 A1 | 3/2007 | Doss |
| 2009/0220444 A1 | 9/2009 | Teckenbrock et al. |
| 2010/0021573 A1 | 1/2010 | Gonzalez et al. |
| 2010/0266480 A1 | 10/2010 | Huang |
| 2010/0330163 A1 | 12/2010 | Soparkar |
| 2011/0076309 A1 | 3/2011 | Misner et al. |
| 2011/0229536 A1 | 9/2011 | Kvitnitsky et al. |
| 2013/0017240 A1 | 1/2013 | Porter et al. |
| 2014/0170086 A1 | 6/2014 | Pan et al. |

FOREIGN PATENT DOCUMENTS

| | | |
|---|---|---|
| CN | 103156073 | 6/2013 |
| CN | 103535536 | 1/2014 |
| DE | 735096 | 5/1943 |
| EP | 0083486 | 12/1982 |
| EP | 0108937 | 5/1984 |
| EP | 0508524 | 10/1992 |
| EP | 0514553 | 11/1992 |
| EP | 0842664 | 5/1998 |
| EP | 1021158 | 7/2000 |
| EP | 1064946 | 1/2001 |
| EP | 1203575 | 5/2002 |
| EP | 1319394 | 6/2003 |
| EP | 1935395 | 6/2008 |
| EP | 1529775 | 5/2011 |
| FR | 2241301 | 3/1975 |
| GB | 2052978 | 2/1981 |
| GB | 2109685 | 6/1983 |
| GB | 2243775 | 11/1991 |
| JP | S57-158724 | 9/1982 |
| JP | 2004175790 | 6/2004 |
| JP | 2009084201 | 4/2009 |
| JP | 2010132639 | 6/2010 |
| WO | WO86/00004 | 1/1986 |
| WO | WO9917735 | 4/1999 |
| WO | WO0169087 | 9/2001 |
| WO | WO2004054531 | 7/2004 |
| WO | WO2004/064536 | 8/2004 |
| WO | WO2007063507 | 6/2007 |
| WO | WO2011053291 | 5/2011 |
| WO | WO2011/088199 | 7/2011 |
| WO | WO2011/123123 | 10/2011 |
| WO | WO2014/098813 | 6/2014 |
| WO | WO2014/098814 | 6/2014 |
| WO | WO2014/098818 | 6/2014 |
| WO | WO2014/098819 | 6/2014 |
| WO | WO2014/098821 | 6/2014 |
| WO | WO2014/098822 | 6/2014 |
| WO | WO2014/098824 | 6/2014 |
| WO | WO2014/099164 | 6/2014 |
| WO | WO2014/099165 | 6/2014 |
| WO | WO2014/099166 | 6/2014 |
| WO | WO2014/099167 | 6/2014 |
| WO | WO2014098825 | 6/2014 |
| WO | WO2014098826 | 6/2014 |
| WO | WO2014098828 | 6/2014 |
| WO | WO2014098829 | 6/2014 |
| WO | WO2014099039 | 6/2014 |
| WO | WO2014099226 | 6/2014 |
| WO | WO2014204439 | 12/2014 |

OTHER PUBLICATIONS

Deschaume et al., "Interactions of aluminum hydrolytic species with biomolecules," New Journal of Chemistry, 2008, 32:1346-1353.

European Food Safety Authority, "Scientific Opinion on the safety and efficacy of tetra-basic zinc chloride for all animal species," EFSA Journal, 2012, 10(5):2672.

Hartwell et al., "Preparation and characterization of tyrosine and lysine metal chelate polyesters and polyamides", J. of the American Chem. Society, Mar. 1970, 92(5):1284-1289.

International Search Report and Written Opinion for International Application No. PCT/US2012/070489 mailed on Oct. 22, 2013.

International Search Report and Written Opinion for International Application No. PCT/US2012/070492 mailed on Oct. 22, 2013.

International Search Report and Written Opinion for International Application No.PCT/US2012/070498 mailed on Sep. 4. 2013.

International Search Report And Written Opinion for International Application No. PCT/US2012/070501 mailed on Oct. 21, 2013.

International Search Report and Written Opinion for International Application No. PCT/US2012/070505 mailed on Nov. 20, 2013.

International Search Report and Written Opinion for International Application No. PCT/US2012/070506 mailed on Oct. 14, 2013.

International Search Report and Written Opinion for International Application No. PCT/US2012/070513 mailed on Oct. 14, 2013.

International Search Report and Written Opinion for International Application No. PCT/US2012/070521 mailed on Sep. 30, 2013.

International Search Report and Written Opinion for International Application No. PCT/US2012/070525 mailed on Sep. 27, 2013.

International Search Report and Written Opinion for International Application No. PCT/US2012/070528 mailed on Sep. 30, 2013.

International Search Report and Written Opinion for International Application No. PCT/US2012/070534 mailed on Sep. 26, 2013.

International Search Report and Written Opinion for International Application No. PCT/US2012/070537 mailed on Oct. 11, 2013.

International Search Report and Written Opinion for International Application No. PCT/US2013/046268 mailed on Apr. 22, 2014.

International Search Report and Written Opinion for International Application No. PCT/US2013/050845 mailed on Aug. 13, 2014.

International Search Report and Written Opinion for International Application No. PCT/US2013/068852 mailed on Nov. 10, 2014.

(56) References Cited

OTHER PUBLICATIONS

International Search Report and Written Opinion for International Application No. PCT/US2013/068854 mailed on Oct. 20, 2014.
International Search Report and Written Opinion for International Application No. PCT/US2013/068859 mailed on Aug. 4, 2014.
International Search Report and Written Opinion for International Application No. PCT/US2013/068860 mailed on Oct. 22, 2014.
International Search Report and Written Opinion for International Application No. PCT/US2013/070932 mailed on Jul. 24, 2014.
International Search Report and Written Opinion for International Application No. PCT/US2014/042947 mailed on Aug. 22, 2014.
International Search Report and Written Opinion for International Application No. PCT/US2014/042948 mailed on Aug. 26, 2014.
International Search Report and Written Opinion for International Application No. PCT/US2014/043051 mailed on Feb. 18, 2015.
Kondrot, "The Importance of Zinc," http:/www.healingtheeye.com/Articles/zinc.html, Feb. 21, 2012.
Liang et al., "In vitro scratch assay: a convenient and inexpensive method for analysis of cell migration in vitro," Nature Protocols, 2007, 2(2):329-333.
Liu et al., "The research on zinc coordination No. 5 odd structure in zinc complex with L -lysine," J. Molecular Science, 2000, 16(2):114-117, abstract only in English.
Lu et al, "Albumin as a zinc carrier: properties of its high-affinity zinc-binding site". Biochem. Soc. Trans., 2008, 36:1317-1321.
Lynch, "Zinc in the mouth, its interactions with dental enamel and possible effects on caries: a review of the literature," Int. Dent. J., Aug. 2011, Suppl 3:46-54.
Mavromichalis et al., "Growth-promoting efficacy of pharmacological doses of tetrabasic zinc chloride in diets for nursery pigs," Canadian Journal of Animal Science, pp. 387-391, Jan. 2001.
McAuliffe et al., "Metal complexes of sulphur-containing amino acids," Inorganica Chimica Acta Reviews, Dec. 1972, 6:103-121.
Moore et al., "Antibacterial activity of gutta-percha cones attributed to the zinc oxide component," Oral Surgery, 1982, 53:508-517.
Mosmann, "Rapid colorimetric assay for cellular growth and survival: Application to proliferation and cytotoxicity assays," J. Immunol. Methods, 1983, 65:55-63.
Pashley et al. Dentin permeability effects of desensitizing dentifrices in vitro. J Periodontol. 1984;55(9):522-525.
Prasad, "Zinc:role in immunity, oxidative stress and chronic inflammation," Current Opinion in Clinical Nutrition and Metabolic Care, 2009, 12:646-652.
Rigano, L., Zinc Lauryl Ether Sulphate—A New Approach to Skin Care, SOFW Journal, Apr. 2004, 128:26-33.
Schmetzer et al., "Wulfingite, $\epsilon$-Zn(OH)2, and simonkolleite, Zn5(OH)8Cl2•H2O, two new minerals from Richelsdorf, Hesse, F.R.G.," N. Jb. Miner. Mh., Apr. 1985, pp. 145-154.
Seil et al., "Antibacterial effect of zinc oxide nanoparticles combined with ultrasound," Nanotechology,2012, 23:495101.
Soderling et al., "Betaine-containing toothpaste relieves subjective symptoms of dry mouth," Acta Odontol. Scand., Apr. 1998, 56(2):65-9.
Stewart et al., "Interdomain zinc site on human albumin," PNAS, 2003, 100(7):3701-3706.
Tian et al., "Using DGGE profiling to develop a novel culture medium suitable for oral microbial communities," Molecular Oral Microbiology, 2010, 25(5):357-367.
Twetman et al., 2003, "Caries-preventative effect of fluoride toothpaste a systematic review," Acta Odontol Scand., Dec. 2003, 61(6):347-55.
Wachi et al., "Antibacterial compsn. Zinc oxide—solubilized by amino acid, amino acid hydrochloride and/or amino acid alkali metal salt," Sep. 1982, vol. 1982(45).
Wallhausser et al., "Antimicrobial Preservatives in Europe: Experience with preservatives used in pharmaceuticals and cosmetics," Develop. Biol. Standard, 1974, 24:9-28.
Yao et al., "An investigation of zirconium(IV)-glycine(CP-2) hybrid complex in bovine serum albumin protein matrix under varying conditions," J. of Materials Chemistry, 2011, 21:19005-19012.
Yousef et al., "In vitro antibacterial activity and minimun inhibitory concentration of zinc oxide and nano-particle zinc oxide against pathogenic strains," J. of Health Sciences, 2012,2(4);38-42.
Zhu et al., "Synthesis and Crystal Structure of [Zn+{H2N(CH2)4CH(NH2)COONa}2SO4-] •H20," Chinese Science Bulletin, Sep. 1990, 35(18):1521-1525.

\* cited by examiner

ZINC AMINO ACID HALIDE COMPLEX WITH CYSTEINE

CROSS REFERENCE TO RELATED APPLICATIONS

This application is a continuation in part of PCT/US2013/46268, filed on 18 Jun. 2013; PCT/US2012/70489, filed on 19 Dec. 2012; PCT/US2012/70492, filed on 19 Dec. 2012; PCT/US2012/70498, filed on 19 Dec. 2012; PCT/US2012/70506, filed on 19 Dec. 2012; PCT/US2012/70513, filed on 19 Dec. 2012; PCT/US2012/70505, filed on 19 Dec. 2012; PCT/US2012/70501, filed on 19 Dec. 2012; PCT/US2012/70521, filed on 19 Dec. 2012; PCT/US2012/70534, filed on 19 Dec. 2012; PCT/US2012/70537, filed on 19 Dec. 2012; PCT/US2012/70525, filed on 19 Dec. 2012; and PCT/US2013/50845, filed on 17 Jul. 2013, all of which are incorporated herein by reference.

BACKGROUND

Conventional antiperspirants comprising salts of aluminum or aluminum/zirconium are known. These salts function as antiperspirants by forming polymeric complexes which can plug pores, thereby blocking sweat release. There is a need for additional antiperspirant active agents that provide molecular weight complexes of a size capable of plugging pores to block sweat, that provide deodorant/antibacterial efficacy, and that are less irritating to the skin than the acidic salts in conventional antiperspirants. There is also a need for alternative antibacterial and skin protective agents for use in liquid hand soaps and body washes. Finally, there is a need for agents in oral care products which can whiten and strengthen teeth, retard erosion, and inhibit bacteria and plaque.

BRIEF SUMMARY

Provided is a composition comprising a zinc amino acid halide complex ("ZXH", wherein X refers to an amino acid or trialkylglycine, "TAG") in combination with cysteine, which complex is stable and soluble in concentrated aqueous solution, but which provides a relatively acid-stable precipitate comprising a complex of zinc (e.g., zinc oxide) and cysteine upon dilution. The unusual and unexpected properties of this material allow delivery of a stable zinc complex to the skin or teeth, making it useful in personal care products, e.g., antiperspirant products and liquid hand and body soaps, as well as in oral care products, e.g. mouthwash or dentifrice.

In one embodiment, the zinc amino acid halide complex (ZXH) is formed by reacting zinc oxide and a halide salt of a basic amino acid to obtain a complex having the general formula:

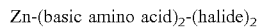

Zn-(basic amino acid)$_2$-(halide)$_2$

In one embodiment, the zinc amino acid halide complex (ZAH) is a zinc-lysine-chloride complex, e.g., formed from a mixture of zinc oxide and lysine hydrochloride, having the formula: $[Zn(C_6H_{14}N_2O_2)_2Cl]^+Cl^-$. This particular zinc-lysine-chloride complex is sometimes referred to herein as "ZLC". In this complex, $Zn^{2+}$ is coordinated by two lysine ligands with two N atoms from $NH_2$ groups and two O atoms from carboxylic groups in an equatorial plane. It displays a distorted square-pyramidal geometry with the apical position occupied by a $Cl^-$ atom. This novel structure gives rise to a positive cation moiety, to which a $Cl^-$ anion is combined to form an ionic salt.

ZLC may exist in solution of the cationic ($[Zn(C_6H_{14}N_2O_2)_2Cl]^+$) and the chloride anion, or may be a solid salt, e.g., a crystal, optionally in mono- or dihydrate form, e.g., as a monohydrate crystal having a powder x-ray diffraction pattern with major peaks having a relative intensity and spacing substantially as depicted in FIG. 1 of PCT/US2012/70498.

Other complexes of zinc and amino acid are possible, and the precise form is dependent in part on the molar ratios of the precursor compounds, e.g., if there is limited halide, halide-free complexes may form, e.g. $ZnLys_2$, having a pyramid geometry, with the equatorial plane that is same as the above compound (Zn is bound to two oxygen and two nitrogen atoms from different lysines), wherein the top of the pyramid is occupied by a Cl atom. Under particular conditions, zinc oxide can also react with lysine and/or lysine HCl to form a clear solution of Zn-lysine-chloride complex ($ZnLys_3Cl_2$), wherein $Zn^{2+}$ is located in an octahedral center coordinated with two oxygen and two nitrogen atoms in the equatorial plane coming from two lysine's carboxylic acids and amine groups respectively. The zinc in this complex is also coordinated to the third lysine via its nitrogen and carboxylic oxygen, at the apical position of the metal geometry. Also, zinc can be provided from other sources than ZnO. Surprisingly, however, we have determined however that the stabilization effect of the cysteine is most effective for complexes having the formula Zn-(basic amino acid)$_2$-(halide)$_2$, thus the combination of the zinc and amino acid halide is preferably controlled to provide this complex as the dominant form.

The zinc X halide complexes, e.g. ZLC, have key features (e.g., conductivity, hydrolysis reaction and protein flocculation) which make it competitive with commercial antiperspirant salts. Like conventional aluminum or aluminum-zirconium antiperspirant salts, the ZXH forms precipitates under sweat conditions that can plug the pores and block sweat release. The mechanism is unusual. As the amount of water increases, rather than going into or remaining in solution as the solution becomes more dilute, as would typically be the case for an ionic complex, the ZXH hydrolyzes, to provide a relatively insoluble zinc oxide precipitate, thereby permitting further plugging of the pores and/or controlled deposition of zinc oxide on the skin. The zinc is moreover antibacterial, and so in addition to providing a precipitate which blocks sweat release from the pores, it provides a deodorant benefit by reducing odor-causing bacteria. Finally, the ZXH may be provided in a formulation which is approximately pH neutral, which is less irritating to the skin and less damaging to clothing than the currently-used aluminum or aluminum-zirconium antiperspirant salts, which are quite acidic in formulation, or current deodorant formulations, which typically contain high levels of alkali fatty acid salts and may be quite basic.

Zinc oxide is soluble at low pH, however, and as sweat has a pH of 5-6, the sweat can reduce the levels of precipitation of the zinc oxide compared to precipitation levels at neutral pH. Moreover, the sweat can gradually dissolve the depositions, reducing the duration of action of the formulation. We have surprisingly discovered that this problem can be ameliorated by co-formulating the product with cysteine. The cysteine and the zinc salt together form a precipitate upon use and dilution with sweat, which precipitate is resistant to acid. The formulation comprising ZXH together with cysteine thus has enhanced efficacy as an antiperspirant. Moreover, the cysteine helps stabilize the ZXH in the formulation prior to administration.

In another embodiment, the ZXH/cysteine combination is also useful in liquid hand soaps and body washes.

In yet another embodiment, the ZXH/cysteine combination is useful in oral care products, for example dentifrice or mouth rinse. A formulation comprising the ZXH/cysteine combination provides an effective concentration of zinc ions to the enamel, thereby protecting against erosion, reducing bacterial colonization and biofilm development, and providing enhanced shine to the teeth. Moreover, upon use, the formulation is diluted and provides a stabilized precipitate that plugs the dentinal tubules, thereby reducing the sensitivity of the teeth. While providing efficient delivery of zinc in comparison to formulations with insoluble zinc salts, the formulations comprising the ZXH/cysteine combination do not exhibit the poor taste and mouthfeel, poor fluoride delivery, and poor foaming and cleaning associated with conventional zinc-based oral care products using soluble zinc salts.

Provided is a composition comprising (i) a zinc amino X halide complex (ZXH), e.g., $[Zn(C_6H_{14}N_2O_2)_2Cl]^+Cl^-$ (ZLC), and (ii) cysteine in free or in orally or cosmetically acceptable salt form. The compositions may be oral care products, e.g., dentifrice or mouth rinse, or personal care products, such as antiperspirants, liquid hand soap or body wash, and skin lotions, creams and conditioners. Further provided are methods of using such compositions, e.g., methods of reducing sweat comprising applying the composition to skin, methods of killing bacteria comprising contacting the bacteria with the composition, and methods of treating or reducing dental hypersensitivity, erosion, and plaque, comprising applying the composition to the teeth, as well as methods of making such compositions.

Further areas of applicability of the present invention will become apparent from the detailed description provided hereinafter. It should be understood that the detailed description and specific examples, while indicating the preferred embodiment of the invention, are intended for purposes of illustration only and are not intended to limit the scope of the invention.

DETAILED DESCRIPTION

The following description of the preferred embodiment(s) is merely exemplary in nature and is in no way intended to limit the invention, its application, or uses.

As used throughout, ranges are used as shorthand for describing each and every value that is within the range. Any value within the range can be selected as the terminus of the range. In addition, all references cited herein are hereby incorporated by referenced in their entireties. In the event of a conflict in a definition in the present disclosure and that of a cited reference, the present disclosure controls.

Unless otherwise specified, all percentages and amounts expressed herein and elsewhere in the specification should be understood to refer to percentages by weight. The amounts given are based on the active weight of the material.

The zinc (amino acid or TAG) halide complex, i.e., ZXH, can be formed by reacting one or more zinc compounds (e.g., zinc oxide, zinc hydroxide, zinc chloride . . . etc., but tetrabasic zinc chloride is specifically excluded) and a halide salt of a basic amino acid to obtain a complex having the general formula:

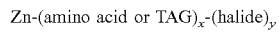

$$Zn\text{-(amino acid or TAG)}_x\text{-(halide)}_y$$

wherein x is 1-3 and y is 1-3.

In one embodiment, the ZXH is a zinc amino acid halide complex ("ZAH") such as a zinc-lysine-chloride complex ("ZLC"), e.g., formed from a mixture of zinc oxide and lysine hydrochloride, having the formula $[Zn(C_6H_{14}N_2O_2)_2Cl]^+Cl^-$. In this complex, $Zn^{2+}$ is coordinated by two lysine ligands with two N atoms from $NH_2$ groups and two O atoms from carboxylic groups in an equatorial plane. Not wishing to be bound by theory, it is believed that it displays a distorted square-pyramidal geometry with the apical position occupied by a $Cl^-$ atom. This structure gives rise to a positive cation moiety, to which a $Cl^-$ anion is combined to form an ionic salt.

In another embodiment, the trialkylglycine (TAG) is $C_1$-$C_4$ alkylglycine or trimethylglycine.

ZLC may exist in solution of the cationic ($[Zn(C_6H_{14}N_2O_2)_2Cl]^+$) and the chloride anion, or may be a solid salt, e.g., a crystal, optionally in mono- or dihydrate form, e.g., as a monohydrate crystal having a powder x-ray diffraction pattern with major peaks having a relative intensity and spacing and spacing substantially as depicted in FIG. 1 of PCT/US2012/70498.

Other complexes of zinc and amino acid are possible, and the precise form is dependent in part on the molar ratios of the precursor compounds, e.g., if there is limited halide, halide-free complexes may form, e.g. $ZnLys_2$, having a pyramid geometry, with the equatorial plane that is same as the above compound (Zn is bound to two oxygen and two nitrogen atoms from different lysines), wherein the top of the pyramid is occupied by a Cl atom. Under particular conditions, zinc oxide can also react with lysine and/or lysine-HCl to form a clear solution of Zn-lysine-chloride complex ($ZnLys_3Cl_2$), wherein $Zn_{2+}$ is located in an octahedral center coordinated with two oxygen and two nitrogen atoms in the equatorial plane coming from two lysine's carboxylic acids and amine groups respectively. The zinc in this complex is also coordinated to the third lysine via its nitrogen and carboxylic oxygen, at the apical position of the metal geometry. The ZXH complexes, e.g. ZLC, have key features (e.g., conductivity, hydrolysis reaction and protein flocculation) which make it competitive with commercial antiperspirant salts. Like conventional aluminum or aluminum-zirconium antiperspirant salts, the ZXH forms precipitates that can plug the pores and block sweat release. As the amount of water increases, the ZXH hydrolyzes to distribute a relatively insoluble zinc-containing precipitate. The precipitate typically contains one or more of zinc oxide, zinc cysteine, zinc hydroxide, or other zinc-containing compounds. This precipitate is unique in that it will allow plugging of pores on the skin. Furthermore, this reaction is atypical since, in most cases, dilution will increase the solubility of an ionic complex. Additionally, zinc is antibacterial, so it provides a precipitate which blocks sweat release from the pores while also it providing a deodorant benefit by reducing odor-causing bacteria.

It is important to note that zinc oxide is soluble at low pH, and as sweat has a pH of 5-6, the sweat can reduce the levels of precipitation of the zinc oxide compared to precipitation levels at neutral pH. Moreover, the sweat can gradually dissolve the depositions, reducing the duration of action of the formulation. This problem can be ameliorated by co-formulating the product with cysteine. The cysteine and the ZHX together form a precipitate. Upon use and dilution with sweat, the precipitate is more resistant to acid than ZHX alone. The formulation comprising ZXH together with cysteine thus has enhanced efficacy as an antiperspirant.

Provided is, in a first embodiment, a composition (Composition 1) comprising (i) a zinc amino acid or TAG halide complex and (ii) cysteine in free or in orally or cosmetically acceptable salt form, e.g., 1.1. Composition 1 wherein the zinc (amino acid or TAG) halide is formed from precursors, wherein the precursors are a zinc ion source, an amino acid source or TAG source, and a halide source, wherein the halide source can be part of the zinc ion source, the amino acid source or trialkylglycine source, or a halogen acid.

1.2. Composition 1 or 1.1 wherein the zinc ion source is at least one of zinc oxide, zinc chloride, zinc carbonate, zinc nitrate, zinc citrate, and zinc phosphate.

1.3. Composition 1.1 or 1.3 wherein the amino acid source is at least one of a basic amino acid, lysine, arginine, glycine.

1.4. Any of the foregoing compositions, wherein the trialkyl glycine is a $C_1$-$C_4$ alkyl glycine or trimethyl glycine.

1.5. Any of the foregoing Compositions wherein the zinc amino acid halide is made by combining zinc oxide with an amino acid hydrohalide.

1.6. Any of the foregoing Compositions wherein the zinc amino acid halide has the formula $Zn(Amino\ Acid)_2Hal_2$ or $Zn(Amino\ Acid)_3Hal_2$, wherein Zn is a divalent zinc ion and Hal is a halide ion.

1.7. Any of the foregoing Compositions wherein the zinc amino acid halide complex is $[Zn(C_6H_{14}N_2O_2)_2Cl]^+Cl^-$ (sometimes referred to herein as "ZLC"), and wherein when the complex is in crystalline form, e.g. in hydrate form, e.g. a monohydrate or dihydrate, e.g., having a structure wherein the Zn cation is coordinated by two lysine ligands with two nitrogen atoms from alpha $NH_2$ groups of the two lysine ligands and two oxygen atoms from carboxylic groups of the two lysine ligands in an equatorial plane, having a distorted square-pyramidal geometry with the apical position occupied by a chlorine atom, to form a positive cation moiety, with which a chloride anion is combined to form an ionic salt; for example a crystal having a powder X-ray diffraction pattern substantially corresponding to one of the two patterns depicted in FIG. 1 of PCT/US2012/70498. [By "substantially corresponding" is meant a correspondence indicating to one of skill in the art that the crystal is the same as or is predominantly composed of the ZLC crystal, e.g., based on the overall pattern of relative intensity and spacing of the peaks, taking into account instrumental and sample variation, e.g., variations in the wavelength and intensity of the x-ray source and the purity of the sample.]

1.8. Composition 1 or 1.1 wherein the zinc-amino acid-halide complex is $[Zn(C_6H_{14}N_2O_2)_2Cl]^+Cl^-$ (sometimes referred to herein as "ZLC"), optionally in hydrate form, e.g. a complex formed from a mixture of zinc oxide and lysine hydrochloride, e.g., in a molar ratio of ZnO: Lysine.HCl of 1:1 to 3:1, e.g., 2:1.

1.9. Any of the foregoing Compositions which upon dilution with water, provides a precipitate comprising zinc oxide in complex with cysteine, and optionally additionally comprising zinc oxide, zinc carbonate, and mixtures thereof.

1.10. Any of the foregoing Compositions wherein the total amount of zinc present in the composition is 0.2 to 8% by weight of the composition.

1.11. Any of the foregoing compositions wherein the ratio of zinc to cysteine is from 5:1 to 10:1 by weight.

1.12. Any of the foregoing compositions, wherein the cysteine is cysteine hydrohalide, optionally cysteine hydrochloride.

1.13. Any of the foregoing compositions wherein the pH of the formulation is 6-8, e.g., 5-7.5, e.g., approximately neutral.

1.14. Any of the foregoing compositions further comprising an orally or cosmetically acceptable carrier.

1.15. Any of the foregoing compositions further comprising an orally or cosmetically acceptable carrier, and which is an oral care product selected from dentifrice or mouthwash, or a personal care product, selected from antiperspirants, deodorants, liquid hand soap, body wash, dermal lotions, dermal creams, and dermal conditioners.

1.16. Any of the foregoing compositions further comprising an orally or cosmetically acceptable carrier that comprises less than 10% water, e.g., less than 5% water, e.g., is substantially anhydrous.

1.17. Any of the foregoing compositions wherein the composition comprises not more than 85% water.

Provided is a method of making composition 1, et seq. comprising (i) combining a zinc ion source, an amino acid source, and a halide source (wherein the halide source can be part of the zinc ion source, the amino acid source, or a halogen acid), in a fluid (e.g., aqueous) medium, optionally isolating the complex thus formed in solid form, combining the complex with cysteine, or (ii) combining a zinc amino acid halide complex and cysteine. The mixture can optionally be combined with a cosmetically acceptable carrier.

Provided is a composition (Composition 2) which is an antiperspirant or deodorant product comprising (i) a zinc amino acid halide complex and (ii) cysteine in free or in cosmetically acceptable salt form, together with a cosmetically acceptable carrier, e.g. in accordance with any of the scopes of Composition 1, et seq., e.g.

2.1. Composition 2 which, upon use and contact with sweat, provides a precipitate to the skin, comprising zinc oxide in complex with cysteine, and optionally additionally comprising zinc oxide, zinc carbonate, and mixtures thereof.

2.2. Composition 2 or 2.1 wherein zinc amino acid halide complex is $[Zn(C_6H_{14}N_2O_2)_2Cl]^+Cl^-$ (sometimes referred to herein as "ZLC"), optionally in hydrate form.

2.3. Composition 2 or 2.1 wherein the cosmetically acceptable carrier comprises one or more ingredients selected from water-soluble alcohols (such as $C_{2-8}$ alcohols including ethanol); glycols (including propylene glycol, dipropylene glycol, tripropylene glycol and mixtures thereof); glycerides (including mono-, di- and triglycerides); medium to long chain organic acids, alcohols and esters; surfactants (including emulsifying and dispersing agents); additional amino acids; structurants (including thickeners and gelling agents, for example polymers, silicates and silicon dioxide); emollients; fragrances; and colorants (including dyes and pigments).

2.4. Composition 2, 2.1, or 2.2 wherein the composition is in the form of an antiperspirant stick, an aerosol antiperspirant spray, or a liquid roll-on antiperspirant.

Also provided are methods of reducing perspiration comprising applying an antiperspirant effective amount of any of Composition 2, et seq. to the skin, methods of reducing body odor comprising applying a deodorant-effective amount of any of Composition 2, et seq. to the skin, and methods of killing bacteria comprising contacting the bacteria with contacting with any of Composition 2, et seq. For example, provided is (i) a method for controlling perspiration comprising applying to skin an antiperspirant effective amount of a formulation of any embodiment embraced or specifically described herein, e.g., any of Composition 2, et seq.; and (ii) a method for controlling odor from perspiration or bacteria on the skin, comprising applying to skin a deodorant effective amount of a formulation of any embodiment embraced or specifically described herein, e.g., any of Composition 2, et seq.

Provided is a method of making an antiperspirant or deodorant comprising (i) a zinc amino acid halide and (ii) cysteine in free or cosmetically acceptable salt form, e.g., any of Composition 2, et seq. comprising combining zinc amino acid halide, cysteine and a cosmetically acceptable carrier.

Also provided is (i) the use of any of Composition 2, et seq. to kill bacteria, reduce perspiration, and/or reduce body odor; and (iii) any of Composition 2, et seq. for use in killing bacteria, reducing perspiration, and/or reducing body odor.

Also provided is the use of cysteine in the manufacture of an antiperspirant or deodorant formulation, e.g., a formulation according to any of Composition 2, et seq.

In making Composition 2, et seq. the zinc amino acid halide and cysteine in free or cometically acceptable salt form can be incorporated into a suitable, cosmetically acceptable base, for example a stick, roll-on, spray or aerosol, for application to the underarm. Following application, in the presence of charged molecules such as proteins found on the skin, the salt will flocculate, forming plugs which block sweat release. Additional water from sweat can moreover dilute the formulation, causing the complex to decompose, resulting in a precipitate composed primarily of zinc oxide in complex with cysteine, which can reduce sweat and odor as described above.

As used herein, the term antiperspirant can refer generally to any product that can form a plug in a pore to reduce sweating, including those materials classified as antiperspirants by the Food and Drug Administration under 21 CFR part 350. It is understood that antiperspirants may also be deodorants, particularly in the case of the described compositions, as zinc has antibacterial properties and thus inhibits odor-causing bacteria on the skin.

Also provided is a composition (Composition 3) which is a personal care product selected from liquid hand soap, body wash, dermal lotions, dermal creams, and dermal conditioners comprising (i) a zinc (amino acid or TAG) halide complex and (ii) cysteine in free or cosmetically acceptable salt form, together with a cosmetically acceptable carrier, e.g. in accordance with any of the scopes of Composition 1, et seq.

3.1. Composition 3 which, upon use with water, provides a precipitate to the skin, comprising zinc oxide in complex with cysteine, and optionally additionally comprising zinc oxide, zinc carbonate, and mixtures thereof.

3.2. Composition 3 or 3.1 comprising the zinc amino acid halide complex in an amount of 1 to 10% by weight of the composition.

2.5. Any of the foregoing compositions wherein the zinc amino acid halide complex is $[Zn(C_6H_{14}N_2O_2)_2Cl]^+Cl^-$ (sometimes referred to herein as "ZLC"), optionally in hydrate form.

3.3. Any of the foregoing compositions, wherein a total amount of zinc present in the composition is 0.1 to 8 weight %, optionally 0.1 to 2 or 0.1 to 1 weight %.

3.4. Any of the foregoing compositions, wherein the cysteine is cysteine hydrohalide, optionally cysteine hydrochloride.

3.5. Any of the foregoing compositions wherein the cosmetically acceptable carrier comprises one or more ingredients selected from water-soluble alcohols (such as $C_{2-8}$ alcohols including ethanol); glycols (including propylene glycol, dipropylene glycol, tripropylene glycol and mixtures thereof); glycerides (including mono-, di- and triglycerides); medium to long chain organic acids, alcohols and esters; surfactants (including emulsifying and dispersing agents); additional amino acids; structurants (including thickeners and gelling agents, for example polymers, silicates and silicon dioxide); emollients; fragrances; and colorants (including dyes and pigments).

3.6. Any of the foregoing compositions, wherein the cosmetically acceptable carrier comprises one or more non-ionic surfactants, for example non-ionic surfactants selected from amine oxide surfactants (e.g., fatty acid amides of alkyl amines, for example lauramidopropyldimethylamine oxide, myristamidopropylamine oxide and mixtures thereof), alcohol amide surfactants (e.g., fatty acid amides of alcohol amines, e.g., cocamide MEA (cocomonoethanolamide)), polyethoxylated surfactants (e.g., polyethoxylated derivatives of esters of fatty acids and polyols (for example glycols, glycerols, saccharides or sugar alcohols), for example polysorbates or PEG-120 methyl glucose dioleate), and combinations thereof.

3.7. Any of the foregoing compositions wherein the cosmetically acceptable carrier comprises an anionic surfactant, e.g. selected from sodium lauryl sulfate and sodium ether lauryl sulfate.

3.8. Any of the foregoing compositions wherein the cosmetically acceptable carrier comprises water, an anionic surfactant, e.g., sodium laureth sulfate, a viscosity modifying agent, e.g., acrylates copolymer, and a zwitterionic surfactant, e.g., cocamidopropyl betaine.

3.9. Any of the foregoing compositions wherein the cosmetically acceptable carrier is substantially free of anionic surfactants.

3.10. Any of the foregoing compositions wherein the cosmetically acceptable carrier comprises water, quaternary ammonium agents (e.g. cetrimonium chloride), humectant (e.g. glycerin), and non-ionic surfactant (e.g., selected from amine oxide surfactants (e.g., lauramidopropyldimethylamine oxide myristamidopropylamine oxide and mixtures thereof), alcohol amide surfactants (e.g., cocamide MEA (cocomonoethanolamide)), polyethoxylate surfactants (e.g. PEG-120 methyl glucose dioleate), and combinations thereof).

3.11. Any of the foregoing compositions, wherein the cosmetically acceptable carrier comprises an antibacterially effective amount of a non-zinc antibacterial agent, e.g., an antibacterial agent selected from triclosan, triclocarban, chloroxylenol, herbal extracts and essential oils (e.g. rosemary extract, tea extract, magnolia extract, thymol, menthol, eucalyptol, geraniol, carvacrol, citral, hinokitol, catechol, methyl salicylate, epigallocatechin gallate, epigallocatechin, galtic acid), bisguanide antiseptics (e.g., chlorhexidine, alexidine or octenidine), and quaternary ammonium compounds (e.g., cetylpyridinium chloride (CPC), benzalkonium chloride, tetradecylpyridinium chloride (TPC), N-tetradecyl-4-ethylpyridinium chloride (TDEPC)); and combinations thereof; for example an antibacterially effective amount of benzalkonium chloride.

3.12. Any of the foregoing compositions which has pH 6-8, e.g, is approximately pH neutral.

3.13. Any of the foregoing compositions comprising ingredients as follows:

| Material | Weight % |
| --- | --- |
| Water | 80-95% |
| Quaternary ammonium antibacterial agents, e.g., selected from cetrimonium chloride (cetyl trimethyl ammonium chloride), $C_{12-18}$ alkydimethylbenzyl ammonium chloride (BKC), and combinations thereof | 0.1-4% |
| Humectants, e.g., glycerin | 1-3% |
| Non-ionic surfactant, e.g., selected from amine oxide surfactants (e.g., lauramidopropyldimethylamine oxide myristamidopropylamine oxide and mixtures thereof), alcohol amide surfactants (e.g., cocamide MEA (cocomonoethanolamide)), polyethoxylate surfactants (e.g. PEG-120 methyl glucose dioleate), and combinations thereof | 1-5% |
| Buffering agents and agents to adjust pH | 1-3% |
| Preservatives and/or chelators | 0.1-2% |
| Fragrance and coloring agents | 0.1-2% |
| ZLC | 1-5%, e.g., 3-4% |
| Cysteine | 0.1-1%, e.g. 0.5% |

Also provided are methods of killing bacteria comprising contacting the bacteria with an antibacterially effective amount of a ZLC, e.g., with any of Composition 3, et seq., for example, methods of treating or reducing the incidence of topical skin infections, for example infections by *Staphylococcus aureus* and/or *Streptococcus pyogenes*, as well as to treat or reduce the incidence of acne, comprising washing the skin with an antibacterially effective amount of a ZLC and cysteine, e.g., with any of Composition 3, et seq., and water.

Also provided is a method of making a personal care composition comprising (i) a zinc amino acid halide complex and (ii) cysteine in free or cosmetically acceptable salt form, e.g., any of Composition 3, et seq. comprising combining (i) combining a zinc ion source, an amino acid source, and a halide source (wherein the halide source can be part of the zinc ion source, the amino acid source, or a halogen acid), in a fluid (e.g., aqueous) medium, optionally isolating the complex thus formed in solid form, combining the complex with cysteine, or (ii) combining a zinc amino acid halide complex and cysteine. The zinc amino acid complex and cysteine are combined with a cosmetically acceptable carrier.

Also provided is (i) the use of a zinc amino acid halide complex and cysteine, e.g., any of Compositions 1, et seq., to kill bacteria, to protect the skin, e.g., from bacteria or to provide a visual signal when washing; (ii) the use of a ZLC and cysteine in the manufacture of a composition, any of Compositions 1, et seq., to kill bacteria, to protect the skin, or to provide a visual signal when washing; and (iii) ZLC and cysteine, e.g., any of Compositions 1, et seq., for use to kill bacteria, to protect the skin, or to provide a visual signal when washing.

For example, in one embodiment, the zinc amino acid complex and the cysteine are incorporated into a conventional commercial liquid hand soap (LHS) formulation comprising surfactants and optionally benzalkonium chloride. The salt is found to be compatible with the formula and generates a transparent solution. Upon dilution, however, the combination instantly forms a white precipitate. Thus, zinc amino acid complex and the cysteine in a surfactant base can provide a visual/sensory trigger for the washing process. The precipitate, composed of ZnO stabilized by cysteine, is deposited on skin and thus enhances the antimicrobial effect of the LHS.

Also provided is a composition (Composition 4) which is an oral care product, e.g., a dentifrice or mouth rinse, comprising (i) a zinc (amino acid or TAG) halide complex and (ii) cysteine in free or orally acceptable salt form, together with an orally acceptable carrier, e.g. in accordance with any of the scopes of Composition 1, et seq., e.g.

4.1. Composition 4 in the form of a dentifrice which upon application to the teeth in the presence of water, provides a precipitate to the teeth, comprising zinc oxide in complex with cysteine, and optionally additionally comprising zinc oxide, zinc carbonate, and mixtures thereof.

4.2. Composition 4 or 4.1 in the form of a dentifrice wherein the zinc amino acid halide complex is present in an effective amount, e.g., in an amount of 0.5-4% by weight of zinc, e.g., 1-3% by weight of zinc, and wherein the orally acceptable carrier is a dentifrice base.

4.3. Any of the foregoing compositions wherein the zinc amino acid halide complex is $[Zn(C_6H_{14}N_2O_2)_2Cl]^+Cl^-$ (sometimes referred to herein as "ZLC"), optionally in hydrate form.

4.4. Any of the foregoing compositions 4-4.2 in the form of a dentifrice, wherein the orally acceptable carrier is a dentifrice base comprising an abrasive, e.g., an effective amount of a silica abrasive, e.g., 10-30%, e.g., 20%.

4.5. Any of the foregoing compositions wherein the zinc amino acid halide complex is present in an effective amount, e.g., in an amount of 0.1-3% by weight of zinc, e.g., 0.2-1% by weight of zinc.

4.6. Any of the foregoing compositions, wherein the cysteine is cysteine hydrohalide, optionally cysteine hydrochloride.

4.7. Any of the foregoing compositions further comprising an effective amount of a fluoride ion source, e.g., providing 500 to 3000 ppm fluoride.

4.8. Any of the foregoing compositions further comprising an effective amount of fluoride, e.g., wherein the fluoride is a salt selected from stannous fluoride, sodium fluoride, potassium fluoride, sodium monofluorophosphate, sodium fluorosilicate, ammonium fluorosilicate, amine fluoride (e.g., N'-octadecyltrimethylendiamine-N,N,N'-tris(2-ethanol)-dihydrofluoride), ammonium fluoride, titanium fluoride, hexafluorosulfate, and combinations thereof.

4.9. Any of the preceding compositions comprising an effective amount of one or more alkali phosphate salts, e.g., sodium, potassium or calcium salts, e.g., selected from alkali dibasic phosphate and alkali pyrophosphate salts, e.g., alkali phosphate salts selected from sodium phosphate dibasic, potassium phosphate dibasic, dicalcium phosphate dihydrate, calcium pyrophosphate, tetrasodium pyrophosphate, tetrapotassium pyrophosphate, sodium tripolyphosphate, and mixtures of any of two or more of these, e.g., in an amount of 1-20%, e.g., 2-8%, e.g., ca. 5%, by weight of the composition.

4.10. Any of the foregoing compositions comprising buffering agents, e.g., sodium phosphate buffer (e.g., sodium phosphate monobasic and disodium phosphate).

4.11. Any of the foregoing compositions comprising a humectant, e.g., selected from glycerin, sorbitol, propylene glycol, polyethylene glycol, xylitol, and mixtures thereof, e.g. comprising at least 20%, e.g., 20-40%, e.g., 25-35% glycerin.

4.12. Any of the preceding compositions comprising one or more surfactants, e.g., selected from anionic, cationic, zwitterionic, and nonionic surfactants, and mixtures thereof, e.g., comprising an anionic surfactant, e.g., a surfactant selected from sodium lauryl sulfate, sodium ether lauryl sulfate, and mixtures thereof, e.g. in an amount of from 0.3% to 4.5% by weight, e.g. 1-2% sodium lauryl sulfate (SLS); and/or a zwitterionic surfactant, for example a betaine surfactant, for example cocamidopropylbetaine, e.g. in an amount of from 0.1% to 4.5% by weight, e.g. 0.5-2% cocamidopropylbetaine.

4.13. Any of the preceding compositions further comprising a viscosity modifying amount of one or more of polysaccharide gums, for example xanthan gum or carrageenan, silica thickener, and combinations thereof.

4.14. Any of the preceding compositions comprising gum strips or fragments.

4.15. Any of the preceding compositions further comprising flavoring, fragrance and/or coloring.

4.16. Any of the foregoing compositions comprising an effective amount of one or more antibacterial agents, for example comprising an antibacterial agent selected from halogenated diphenyl ether (e.g. triclosan), herbal extracts and essential oils (e.g., rosemary extract, tea extract, magnolia extract, thymol, menthol, eucalyptol, geraniol, carvacrol, citral, hinokitol, catechol, methyl salicylate, epigallocatechin gallate, epigallocatechin, gallic acid, miswak extract, sea-buckthorn extract), bisguanide antiseptics (e.g., chlorhexidine, alexidine or octenidine), quaternary ammonium compounds (e.g., cetylpyridinium chloride (CPC), benzalkonium chloride, tetradecylpyridinium chloride (TPC), N-tetradecyl-4-ethylpyridinium chloride (TDEPC)), phenolic antiseptics, hexetidine, octenidine, sanguinarine, povidone iodine, delmopinol, salifluor, metal ions (e.g., zinc salts, for example, zinc citrate, stannous salts, copper salts, iron salts), sanguinarine, propolis and oxygenating agents (e.g., hydrogen peroxide, buffered sodium peroxyborate or peroxycarbonate), phthalic acid and its salts, monoperthalic acid and its salts and esters, ascorbyl stearate, oleoyl sarcosine, alkyl sulfate, dioctyl sulfosuccinate, salicylanilide, domiphen bromide, delmopinol, octapinol and other piperidino derivatives, nicin preparations, chlorite salts; and mixtures of any of the foregoing; e.g., comprising triclosan or cetylpyridinium chloride.

4.17. Any of the foregoing compositions comprising an antibacterially effective amount of triclosan, e.g. 0.1-0.5%, e.g. 0.3%.

4.18. Any of the preceding compositions further comprising a whitening agent, e.g., a selected from the group consisting of peroxides, metal chlorites, perborates, percarbonates, peroxyacids, hypochlorites, and combinations thereof.

4.19. Any of the preceding compositions further comprising hydrogen peroxide or a hydrogen peroxide source, e.g., urea peroxide or a peroxide salt or complex (e.g., such as peroxyphosphate, peroxycarbonate, perborate, peroxysilicate, or persulphate salts; for example calcium peroxyphosphate, sodium perborate, sodium carbonate peroxide, sodium peroxyphosphate, and potassium persulfate);

4.20. Any of the preceding compositions further comprising an agent that interferes with or prevents bacterial attachment, e.g., solbrol or chitosan.

4.21. Any of the preceding compositions further comprising a source of calcium and phosphate selected from (i) calcium-glass complexes, e.g., calcium sodium phosphosilicates, and (ii) calcium-protein complexes, e.g., casein phosphopeptide-amorphous calcium phosphate 4.22. Any of the preceding compositions further comprising a soluble calcium salt, selected from calcium sulfate, calcium chloride, calcium nitrate, calcium acetate, calcium lactate, and combinations thereof.

4.23. Any of the preceding compositions further comprising a physiologically or orally acceptable potassium salt, e.g., potassium nitrate or potassium chloride, in an amount effective to reduce dentinal sensitivity.

4.24. Any of the foregoing compositions further comprising an anionic polymer, e.g., a synthetic anionic polymeric polycarboxylate, e.g., wherein the anionic polymer is selected from 1:4 to 4:1 copolymers of maleic anhydride or acid with another polymerizable ethylenically unsaturated monomer; e.g., wherein the anionic polymer is a methyl vinyl ether/maleic anhydride (PVM/MA) copolymer having an average molecular weight (M.W.) of 30,000 to 1,000,000, e.g. 300,000 to 800,000, e.g., wherein the anionic polymer is 1-5%, e.g., 2%, of the weight of the composition.

4.25. Any of the preceding compositions further comprising a breath freshener, fragrance or flavoring.

4.26. Any of the foregoing compositions, wherein the pH of the composition is approximately neutral, e.g., from pH 6 to pH 8 e.g., pH 7.

4.27. Any of the foregoing compositions in the form of an oral gel, wherein the amino acid is lysine and the zinc and lysine form a zinc amino acid halide complex having the chemical structure $[Zn(C_6H_{14}N_2O_2)_2Cl]^+Cl^-$, in an amount to provide 0.1-8%, e.g., 0.5% zinc by weight, and further comprising humectant, e.g., sorbitol, propylene glycol and mixtures thereof, e.g., in an amount of 45-65%, e.g., 50-60%, thickeners, e.g., cellulose derivatives, e.g., selected from carboxymethyl cellulose (CMC), trimethyl cellulose (TMC) and mixtures thereof, e.g., in an amount of 0.1-2%, sweetener and/or flavorings, and water, e.g., an oral gel comprising

| Ingredients | % |
| --- | --- |
| Sorbitol | 40-60%, e.g., 50-55% |
| ZLC | to provide 0.1-2%Zn, e.g 0.5% Zn |
| Cysteine | 0.02-0.5%, e.g., 0.1% |
| Carboxymethyl cellulose (CMC) and Trimethyl cellulose (TMC) | 0.5-1%, e.g., 0.7% |
| Flavoring and/or sweetener | 0.01-1% |
| Propylene Glycol | 1-5%, e.g., 3.00% |

4.28. Any of the forgoing compositions for use to reduce and inhibit acid erosion of the enamel, clean the teeth, reduce bacterially-generated biofilm and plaque, reduce gingivitis, inhibit tooth decay and formation of cavities, and reduce dentinal hypersensitivity.

Also provided are methods to reduce and inhibit acid erosion of the enamel, clean the teeth, reduce bacterially-generated biofilm and plaque, reduce gingivitis, inhibit tooth decay and formation of cavities, and reduce dentinal hypersensitivity, comprising applying an effective amount of a composition, e.g., any of Composition 4, et seq. to the teeth, and optionally then rinsing with water or aqueous solution sufficient to trigger precipitation of zinc oxide in complex with cysteine from the composition.

Also provided is a method of making an oral care composition comprising (i) a zinc amino acid halide complex and (ii) cysteine free or orally acceptable salt form, e.g., any of Composition 4, et seq. comprising combining (i) combining a zinc ion source, an amino acid source, and a halide source (wherein the halide source can be part of the zinc ion source, the amino acid source, or a halogen acid), in a fluid (e.g., aqueous) medium, optionally isolating the complex thus formed in solid form, combining the complex with cysteine, or (ii) combining a zinc amino acid halide complex and cysteine. The zinc amino acid halide complex and cysteine can be combined with an oral care base, e.g., a dentifrice or mouthwash base.

For example, in various embodiments, provided are methods to (i) reduce hypersensitivity of the teeth, (ii) to reduce plaque accumulation, (iii) reduce or inhibit demineralization and promote remineralization of the teeth, (iv) inhibit microbial biofilm formation in the oral cavity, (v) reduce or inhibit gingivitis, (vi) promote healing of sores or cuts in the mouth, (vii) reduce levels of acid producing bacteria, (viii) to increase relative levels of non-cariogenic and/or non-plaque forming bacteria, (ix) reduce or inhibit formation of dental caries, (x), reduce, repair or inhibit pre-carious lesions of the enamel, e.g., as detected by quantitative light-induced fluorescence (QLF) or electrical caries measurement (ECM), (xi) treat, relieve or reduce dry mouth, (xii) clean the teeth and oral cavity, (xiii) reduce erosion, (xiv) whiten teeth; (xv) reduce tartar build-up, and/or (xvi) promote systemic health, including cardiovascular health, e.g., by reducing potential for systemic infection via the oral tissues, comprising applying any of Compositions 4, et seq. as described above to the oral cavity of a person in need thereof, e.g., one or more times per day. Also provided are Compositions 4, et seq. for use in any of these methods.

Also provided is the use of (i) a zinc amino acid halide complex, and (ii) cysteine in free or orally acceptable salt form in the manufacture of an oral care composition, e.g., in accordance with any of Compositions 4, et seq.

Also provided is the use of (i) a zinc amino acid halide complex, and (ii) cysteine in free or orally acceptable salt form, to reduce and inhibit acid erosion of the enamel, clean the teeth, reduce bacterially-generated biofilm and plaque, reduce gingivitis, inhibit tooth decay and formation of cavities, and/or reduce dentinal hypersensitivity.

Also provided is the use of cysteine in free or orally acceptable salt form to stabilize a zinc amino acid halide complex.

It will be understood that, although the zinc amino acid halide complex may be primarily in the form of a complex, there may be some degree of equilibrium with the salt precursor materials and other ions in the formulation, and further the complex may not be fully dissolved, so that the proportion of material which is actually in complex compared to the proportion in precursor form may vary depending on the precise conditions of formulation, concentration of materials, pH, presence or absence of water, presence or absence of other charged molecules, and so forth.

In one embodiment, the zinc amino acid halide complex is prepared at room temperature by mixing the precursors in an aqueous solution. The in situ formation provides ease of formulation. The precursors can be used instead of first having to form the salt. In another embodiment, the water permitting formation of the salt from the precursor comes from water (e.g., rinsing water, saliva or sweat, depending on the application) that comes into contact with the composition in the course of use.

In some embodiments, the total amount of zinc in the composition is 0.05 to 8% by weight of the composition. In other embodiments, the total amount of zinc is at least 0.1, at least 0.2, at least 0.3, at least 0.4, at least 0.5, or at least 1 up to 8% by weight of the composition. In other embodiments, the total amount of zinc in the composition is less than 5, less than 4, less than 3, less than 2, or less than 1 to 0.05% by weight of the composition. For example, the zinc content may be 2-3%.

In certain embodiments, the composition is anhydrous. By anhydrous, there is less than 5% by weight water, optionally less than 4, less than 3, less than 2, less than 1, less than 0.5, less than 0.1 down to 0% by weight water. When provided in an anhydrous composition, precursors of zinc amino acid halide complex, e.g., zinc oxide and lysine hydrochloride, will not significantly react. When contacted with a sufficient amount of water, the precursors will then react to form the desired salt, e.g., ZLC, which upon further dilution with use forms the desired precipitate on the skin or teeth.

Amino Acids:

The amino acid in the zinc amino acid halide complex can a basic amino acid. By "basic amino acid" is meant the naturally occurring basic amino acids, such as arginine, lysine, and histidine, as well as any basic amino acid having a carboxyl group and an amino group in the molecule, which is water-soluble and provides an aqueous solution with a pH of 7 or greater. Accordingly, basic amino acids include, but are not limited to, arginine, lysine, citrulline, ornithine, creatine, histidine, diaminobutanoic acid, diaminoproprionic acid, salts thereof or combinations thereof. In a particular embodiment, the basic amino acid is lysine. The basic amino acids for use in making zinc amino acid halide complex are generally provided in the form of the halide acid addition salt, e.g., a hydrochloride.

Cysteine:

The compositions also comprise cysteine in free or orally or cosmetically acceptable salt form. By "orally or cosmetically acceptable salt form" is meant a salt form which is safe for administration to the oral cavity or skin respectively in the concentrations provided, and which does not interfere with the biological activity of the zinc. In a particular embodiment, the cysteine is administered in free form. Wherever weights are given for amounts of amino acids in formulations herein, the weights are generally provided in terms of the weight of the free acid unless otherwise noted. In some embodiments, the cysteine is a cysteine hydrohalide, such as cysteine hydrochloride.

In compositions comprising an orally or cosmetically acceptable carrier, the carrier represents all other materials in the composition other than zinc amino acid halide complex (including precursors) and the cysteine. The amount of carrier is thus the amount to reach 100% by adding to the weight of zinc amino acid halide complex (including precursors) and the protein. By "orally acceptable carrier" is meant a carrier which is suitable for use in an oral care product, consisting of ingredients which are generally recognized as safe for use in amounts and concentrations as provided in a dentifrice or mouth rinse, for example. By "cosmetically acceptable carrier" is meant a carrier which is suitable for use in a product for topical use on the skin, consisting of ingredients which are generally recognized as safe for use in amounts and concentrations as provided in a liquid hand soap or body wash, or in an antiperspirant product, for example. Excipients for use in the compositions thus may include for example excipients which are "Generally Recognized as Safe" (GRAS) by the United States Food and Drug Administration.

Personal Care Formulations:

The term "cosmetically acceptable carrier" thus refers to any formulation or carrier medium that provides the appropriate delivery of an effective amount of the complex as defined herein, does not interfere with the effectiveness of the biological activity of the zinc, and is suitable and nontoxic for topical administration to the skin. Representative carriers include water, oils, both vegetable and mineral, soap bases, cream bases, lotion bases, ointment bases and the like, particularly aqueous detergent carriers, for example liquid hand soaps or body washes. In one embodiment, the aqueous soap bases are free of or contain less than one percent of anionic surfactants. In another embodiment, the cosmetically acceptable carrier contains topically acceptable quaternary ammonium compounds. They may additionally include buffers, preservatives, antioxidants, fragrances, emulsifiers, dyes and excipients known or used in the field of drug formulation and that do not unduly interfere with the effectiveness of the biological activity of the active agent, and that is sufficiently non-toxic to the host or patient. Additives for topical formulations are well-known in the art, and may be added to the topical composition, as long as they are pharmaceutically acceptable and not deleterious to the epithelial cells or their function. Further, they should not cause deterioration in the stability of the composition. For example, inert fillers, anti-irritants, tackifiers, excipients, fragrances, opacifiers, antioxidants, gelling agents, stabilizers, surfactant, emollients, coloring agents, preservatives, buffering agents, and other conventional components of topical formulations as are known in the art.

In some cases, the personal care compositions comprise oils or moisturizers, which may not be water soluble and may be delivered in an emulsion system, wherein the zinc-lysine complex would be in the water phase of the emulsion. Surfactants for the emulsion formulations may comprise a combination of nonionic surfactants, for example, one or more surfactants selected from the group consisting of (i) lipophilic surfactants, e.g., having an HLB value of 8 or lower, for example sorbitan-fatty acid esters, such as sorbitan oleates, for example, sorbitan sesquioleate; and (ii) hydrophilic surfactants, e.g., having an HLB of greater than 8, particularly a di- or tri-alkanol amines, such as triethanol amine; b. polyethoxylated surfactants, for example polyethoxylated alcohols (esp. polyethoxylated polyols), polyethoxylated vegetable oils, and polyethoxylated silicones, e.g., polysorbate 80, dimethicone polyethylene oxide, and dimethylmethyl(polyethylene oxide) siloxane. For a water-in-oil emulsion, the overall HLB of the surfactant mixture is (preferably 2-8, i.e., there is typically a higher proportion of lipophilic surfactant; whereas for an oil-in-water emulsion, the overall HLB of the surfactant mixture is preferably 8-16.

The personal care compositions may also comprise suitable antioxidants, substances known to inhibit oxidation. Antioxidants suitable for use in the compositions include, but are not limited to, butylated hydroxytoluene, ascorbic acid, sodium ascorbate, calcium ascorbate, ascorbic palmitate, butylated hydroxyanisole, 2,4,5-trihydroxybutyrophenone, 4-hydroxymethyl-2,6-di-fert-butylphenol, erythorbic acid, gum guaiac, propyl gallate, thiodipropionic acid, dilauryl thiodipropionate, tert-butylhydroquinone and tocopherols such as vitamin E, and the like, including pharmaceutically acceptable salts and esters of these compounds. Preferably, the antioxidant is butylated hydroxytoluene, butylated hydroxyanisole, propyl gallate, ascorbic acid, pharmaceutically acceptable salts or esters thereof, or mixtures thereof. Most preferably, the antioxidant is butylated hydroxytoluene. These materials are available from Ruger Chemical Co, (Irvington, N.J.). When the topical formulations contain at least one antioxidant, the total amount of antioxidant present is from 0.001 to 0.5 wt %, preferably 0.05 to 0.5 wt %, more preferably 0.1%.

The pesonal care compositions may also comprise suitable preservatives. Preservatives are compounds added to a formulation to act as an antimicrobial agent. Among preservatives known in the art as being effective and acceptable in parenteral formulations are benzalkonium chloride, benzethonium, chlorhexidine, phenol, m-cresol, benzyl alcohol, methylparaben, propylparaben, chlorobutanol, o-cresol, p-cresol, chlorocresol, phenytmercuric nitrate, thimerosal, benzoic acid, and various mixtures thereof. See, e.g., Wallhausser, K.-H., Develop. Biol. Standard, 24:9-28 (1974) (S. Krager, Basel). Preferably, the preservative is selected from methylparaben, propylparaben and mixtures thereof. These materials are available from Molex Chemical Co (Philadelphia, Pa.) or Spectrum Chemicals. When the topical formulations contain at least one preservative, the total amount of preservative present is from 0.01 to 0.5 wt %, preferably from 0.1 to 0.5%, more preferably from 0.03 to 0.15. Preferably the preservative is a mixture of methylparaben and proplybarben in a 5/1 ratio. When alcohol is used as a preservative, the amount is usually 15 to 20%.

The personal care compositions may also comprise suitable cheating agents to form complexes with metal cations that do not cross a lipid bilayer. Examples of suitable cheating agents include ethylene diamine tetraacetic acid (EDTA), ethylene glycol-bis(beta-aminoethyl ether)-N,N,N',N'-tetraacetic acid (EGTA) and 8-Amino-2-[(2-amino-5-methylphenoxy)methyl]-6-methoxyquinoline-$N_5$N,N',N'-tetraacetic acid, tetrapotassium salt (QUIN-2), Preferably the chelating agents are EDTA and citric acid. These materials are available from Spectrum Chemicals. When the topical formulations contain at least one chelating agent, the total amount of cheating agent present is from 0.005% to 2.0% by weight, preferably from 0.05% to 0.5 wt %, more preferably 0.1% by weight. Care must be taken that the chelators do not interfere with the zinc complex, for example by binding zinc, but in the formulations tested, low levels of EDTA, for example, have not presented problems.

The personal care compositions may also comprise suitable pH adjusting agents and/or buffers to adjust and maintain the pH of the formulation to a suitable range, e.g., pH 6-8 or approximately neutral pH.

The personal care compositions may also comprise suitable viscosity increasing agents. These components are diffusible compounds capable of increasing the viscosity of a polymer containing solution through the interaction of the agent with the polymer. CARBOPOL ULTREZ 10 may be used as a viscosity-increasing agent. These materials are available from Noveon Chemicals, Cleveland, Ohio. When the topical formulations contain at least one viscosity increasing agent, the total amount of viscosity increasing agent present is from 0.25% to 5.0% by weight, preferably from 0.25% to 1.0 wt %, and more preferably from 0.4% to 0.6% by weight.

Liquid forms, such as lotions suitable for topical administration or suitable for cosmetic application, may include a suitable aqueous or nonaqueous vehicle with buffers, suspending and dispensing agents, thickeners, penetration enhancers, and the like. Solid forms such as creams or pastes or the like may include, for example, any of the following ingredients, water, oil, alcohol or grease as a substrate with surfactant, polymers such as polyethylene glycol, thickeners, solids and the like. Liquid or solid formulations may include enhanced delivery technologies such as liposomes, microsomes, microsponges and the like.

Topical treatment regimens can comprise applying the composition directly to the skin at the application site, from one to several times daily, and washing with water to trigger precipitation of the zinc oxide on the skin.

Formulations can be used to treat, ameliorate or prevent conditions or symptoms associated with bacterial infections, acne, inflammation and the like.

Oral Care Formulations:

The oral care compositions, e.g., Composition 4, et seq. may comprise various agents which are active to protect and enhance the strength and integrity of the enamel and tooth structure and/or to reduce bacteria and associated tooth decay and/or gum disease, including or in addition to the zinc-amino acid-halide complexes. Effective concentration of the active ingredients used herein will depend on the particular agent and the delivery system used. It is understood that a toothpaste for example will typically be diluted with water upon use, while a mouth rinse typically will not be. Thus, an effective concentration of active in a toothpaste will ordinarily be 5-15× higher than required for a mouth rinse. The concentration will also depend on the exact salt or polymer selected. For example, where the active agent is provided in salt form, the counterion will affect the weight of the salt, so that if the counterion is heavier, more salt by weight will be required to provide the same concentration of active ion in the final product. Arginine, where present, may be present at levels from e.g., 0.1 to 20 wt % (expressed as weight of free base), e.g., 1 to 10 wt % for a consumer toothpaste or 7 to 20 wt % for a professional or prescription treatment product. Fluoride where present may be present at levels of e.g., 25 to 25,000 ppm, for example 750 to 2,000 ppm for a consumer toothpaste, or 2,000 to 25,000 ppm for a professional or prescription treatment product. Levels of antibacterial agents will vary similarly, with levels used in toothpaste being e.g., 5 to 15 times greater than used in mouthrinse. For example, a triclosan toothpaste may contain 0.3 wt % triclosan.

The oral care compositions may further include one or more fluoride ion sources, e.g., soluble fluoride salts. A wide variety of fluoride ion-yielding materials can be employed as sources of soluble fluoride in the present compositions. Examples of suitable fluoride ion-yielding materials are found in U.S. Pat. No. 3,535,421, to Briner et al.; U.S. Pat. No. 4,885,155, to Parran, Jr. et al. and U.S. Pat. No. 3,678,154, to Widder et al. Representative fluoride ion sources include, but are not limited to, stannous fluoride, sodium fluoride, potassium fluoride, sodium monofluorophosphate, sodium fluorosilicate, ammonium fluorosilicate, amine fluoride, ammonium fluoride, and combinations thereof. In certain embodiments the fluoride ion source includes stannous fluoride, sodium fluoride, sodium monofluorophosphate as well as mixtures thereof. In certain embodiments, the oral care composition may also contain a source of fluoride ions or fluorine-providing ingredient in amounts sufficient to supply 25 ppm to 25,000 ppm of fluoride ions, generally at least 500 ppm, e.g., 500 to 2000 ppm, e.g., 1000 to 1600 ppm, e.g., 1450 ppm. The appropriate level of fluoride will depend on the particular application. A toothpaste for general consumer use would typically have 1000 to 1500 ppm, with pediatric toothpaste having somewhat less. A dentifrice or coating for professional application could have as much as 5,000 or even 25,000 ppm fluoride. Fluoride ion sources may be added to the compositions at a level of 0.01 wt. % to 10 wt. % in one embodiment or 0.03 wt. % to 5 wt. %, and in another enibodiment 0.1 wt. % to 1 wt. % by weight of the composition in another embodiment. Weights of fluoride salts to provide the appropriate level of fluoride ion will obviously vary based on the weight of the counterion in the salt.

Abrasives:

The oral care compositions, e.g. Composition 4 et seq. may include silica abrasives, and may comprise additional abrasives, e.g., a calcium phosphate abrasive, e.g., trical-cium phosphate ($Ca_3(PO_4)_2$), hydroxyapatite ($Ca_{10}(PO_4)_6(OH)_2$), or dicalcium phosphate dihydrate ($CaHPO_4.2H_2O$, also sometimes referred to herein as DiCal) or calcium pyrophosphate; calcium carbonate abrasive; or abrasives such as sodium metaphosphate, potassium metaphosphate, aluminum silicate, calcined alumina, bentonite or other siliceous materials, or combinations thereof.

Other silica abrasive polishing materials useful herein, as well as the other abrasives, generally have an average particle size ranging between 0.1 and 30 microns, between 5 and 15 microns. The silica abrasives can be from precipitated silica or silica gels, such as the silica xerogels described in U.S. Pat. No. 3,538,230, to Pader et al. and U.S. Pat. No. 3,862,307, to Digiulio. Particular silica xerogels are marketed under the trade name Syloid® by the W. R. Grace & Co., Davison Chemical Division. The precipitated silica materials include those marketed by the J. M. Huber Corp. under the trade name Zeodent®, including the silica carrying the designation Zeodent 115 and 119. These silica abrasives are described in U.S. Pat. No. 4,340,583, to Wason. In certain embodiments, abrasive materials useful in the practice of the oral care compositions include silica gels and precipitated amorphous silica having an oil absorption value of less than 100 cc/100 g silica and in the range of 45 cc/100 g to 70 cc/100 g silica. Oil absorption values are measured using the ASTA Rub-Out Method D281. In certain embodiments, the silicas are colloidal particles having an average particle size of 3 microns to 12 microns, and 5 to 10 microns. Low oil absorption silica abrasives particularly useful in the compositions are marketed under the trade designation Sylodent XWA®, by Davison Chemical Division of W.R. Grace & Co., Baltimore, Md. 21203. Sylodent 650 XWA®, a silica hydrogel composed of particles of colloidal silica having a water content of 29% by weight averaging 7 to 10 microns in diameter, and an oil absorption of less than 70 cc/100 g of silica is an example of a low oil absorption silica abrasive useful in the composition.

Foaming Agents:

The oral care compositions also may include an agent to increase the amount of foam that is produced when the oral cavity is brushed. Illustrative examples of agents that increase the amount of foam include, but are not limited to polyoxyethylene and certain polymers including, but not limited to, alginate polymers. The polyoxyethylene may increase the amount of foam and the thickness of the foam generated by the oral care carrier component of the composition. Polyoxyethylene is also commonly known as polyethylene glycol ("PEG") or polyethylene oxide. The polyoxyethylenes suitable for this composition will have a molecular weight of 200,000 to 7,000,000. In one embodiment the molecular weight will be 600,000 to 2,000,000 and in another embodiment 800,000 to 1,000,000. Polyox® is the trade name for the high molecular weight polyoxyethylene produced by Union Carbide. The polyoxyethylene may be present in an amount of 1% to 90%, in one embodiment 5% to 50% and in another embodiment 10% to 20% by weight of the oral care carrier component of the oral care compositions. Where present, the amount of foaming agent in the oral care composition (i.e., a single dose) is 0.01 to 0.9% by weight, 0.05 to 0.5% by weight, and in another embodiment 0.1 to 0.2% by weight.

Surfactants:

The compositions may contain anionic, cationic, nonionic and/or zwitterionic surfactants, for example:

i. water-soluble salts of higher fatty acid monoglyceride monosulfates, such as the sodium salt of the monosulfated monoglyceride of hydrogenated coconut oil fatty acids such as sodium N-methyl N-cocoyl taurate, sodium cocomonoglyceride sulfate, ii. higher alkyl sulfates, such as sodium lauryl sulfate,
iii. higher alkyl-ether sulfates, e.g., of formula $CH_3(CH_2)_m CH_2(OCH_2CH_2)_n OSO_3X$, wherein m is 6-16, e.g., 10, n is 1-6, e.g., 2, 3 or 4, and X is Na or K, for example sodium laureth-2 sulfate $(CH_3(CH_2)_{10}CH_2(OCH_2CH_2)_2 OSO_3Na)$.
iv. higher alkyl aryl sulfonates such as sodium dodecyl benzene sulfonate (sodium lauryl benzene sulfonate)
v. higher alkyl sulfoacetates, such as sodium lauryl sulfoacetate (dodecyl sodium sulfoacetate), higher fatty acid esters of 1,2 dihydroxy propane sulfonate, sulfocolaurate (N-2-ethyl laurate potassium sulfoacetamide) and sodium lauryl sarcosinate.

By "higher alkyl" is meant, e.g., $C_{6-30}$ alkyl. In particular embodiments, the anionic surfactant is selected from sodium lauryl sulfate and sodium ether lauryl sulfate. The anionic surfactant may be present in an amount which is effective, e.g., >0.01% by weight of the formulation, but not at a concentration which would be irritating to the oral tissue, e.g., <10%, and optimal concentrations depend on the particular formulation and the particular surfactant. For example, concentrations used or a mouthwash are typically on the order of one tenth that used for a toothpaste. In one embodiment, the anionic surfactant is present in a toothpaste at 0.3% to 4.5% by weight, e.g., 1.5%. The compositions may optionally contain mixtures of surfactants, e.g., comprising anionic surfactants and other surfactants that may be anionic, cationic, zwitterionic or nonionic. Generally, surfactants are those which are reasonably stable throughout a wide pH range. Surfactants are described more fully, for example, in U.S. Pat. No. 3,959,458, to Agricola et al.; U.S. Pat. No. 3,937,807, to Haefele; and U.S. Pat. No. 4,051,234, to Gieske et al. In certain embodiments, the anionic surfactants useful herein include the water-soluble salts of alkyl sulfates having 10 to 18 carbon atoms in the alkyl radical and the water-soluble salts of sulfonated monoglycerides of fatty acids having 10 to 18 carbon atoms. Sodium lauryl sulfate, sodium lauroyl sarcosinate and sodium coconut monoglyceride sulfonates are examples of anionic surfactants of this type. In a particular embodiment, the composition, e.g., Composition 4, et seq., comprises sodium lauryl sulfate.

The surfactant or mixtures of compatible surfactants can be present in the composition 0.1% to 5%, in another embodiment 0.3% to 3% and in another embodiment 0.5% to 2% by weight of the total composition.

Note that care must be taken that the anionic surfactants do not interfere with zinc amino acid halide complex or with the activity of the zinc. At relatively low levels and in a relatively low water formulation, the surfactants generally would not have major impact, but higher levels of anionic surfactant, particularly in aqueous formulations, anionic surfactants can be excluded. Cationic and/or nonionic surfactants may be utilized instead.

Tartar Control Agents:

In various embodiments, the compositions comprise an anticalculus (tartar control) agent. Suitable anticalculus agents include without limitation phosphates and polyphosphates (for example pyrophosphates), polyaminopropanesulfonic acid (AMPS), hexametaphosphate salts, zinc citrate trihydrate, polypeptides, polyolefin sulfonates, polyolefin phosphates, diphosphonates. The composton thus may comprise phosphate salts. In particular embodiments, these salts are alkali phosphate salts, i.e., salts of alkali metal hydroxides or alkaline earth hydroxides, for example, sodium, potassium or calcium salts. "Phosphate" as used herein encompasses orally acceptable mono- and polyphosphates, for example, $P_{1-6}$ phosphates, for example monomeric phosphates such as monobasic, dibasic or tribasic phosphate; dimeric phosphates such as pyrophosphates; and multimeric phosphates, e.g., sodium hexametaphosphate. In particular examples, the selected phosphate is selected from alkali dibasic phosphate and alkali pyrophosphate salts, e.g., selected from sodium phosphate dibasic, potassium phosphate dibasic, dicalcium phosphate dihydrate, calcium pyrophosphate, tetrasodium pyrophosphate, tetrapotassium pyrophosphate, sodium tripolyphosphate, and mixtures of any of two or more of these. In a particular embodiment, for example the compositions comprise a mixture of tetrasodium pyrophosphate ($Na_4P_2O_7$), calcium pyrophosphate ($Ca_2P_2O_7$), and sodium phosphate dibasic ($Na_2HPO_4$), e.g., in amounts of ca. 3-4% of the sodium phosphate dibasic and ca. 0.2-1% of each of the pyrophosphates. In another embodiment, the compositions comprise a mixture of tetrasodium pyrophosphate (TSPP) and sodium tripolyphosphate (STPP) ($Na_5P_3O_{10}$), e.g., in proportions of TSPP at 1-2% and STPP at 7% to 10%. Such phosphates are provided in an amount effective to reduce erosion of the enamel, to aid in cleaning the teeth, and/or to reduce tartar buildup on the teeth, for example in an amount of 2-20%, e.g., ca. 5-15%, by weight of the composition.

Flavoring Agents:

The oral care compositions may also include a flavoring agent. Flavoring agents which can be used in the composition include, but are not limited to, essential oils as well as various flavoring aldehydes, esters, alcohols, and similar materials. Examples of the essential oils include oils of spearmint, peppermint, wintergreen, sassafras, clove, sage, eucalyptus, marjoram, cinnamon, lemon, lime, grapefruit, and orange. Also useful are such chemicals as menthol, carvone, and anethole. Certain embodiments employ the oils of peppermint and spearmint. The flavoring agent may be incorporated in the oral composition at a concentration of 0.1 to 5% by weight e.g. 0.5 to 1.5% by weight.

Polymers:

The oral care compositions may also include additional polymers to adjust the viscosity of the formulation or enhance the solubility of other ingredients. Such additional polymers include polyethylene glycols, polysaccharides (e.g., cellulose derivatives, for example carboxymethyl cellulose, or polysaccharide gums, for example xanthan gum or carrageenan gum). Acidic polymers, for example polyacrylate gels, may be provided in the form of their free acids or partially or fully neutralized water soluble alkali metal (e.g., potassium and sodium) or ammonium salts.

Silica thickeners, which form polymeric structures or gels in aqueous media, may be present. Note that these silica thickeners are physically and functionally distinct from the particulate silica abrasives also present in the compositions, as the silica thickeners are very finely divided and provide little or no abrasive action. Other thickening agents are carboxyvinyl polymers, carrageenan, hydroxyethyl cellulose and water soluble salts of cellulose ethers such as sodium carboxymethyl cellulose and sodium carboxymethyl hydroxyethyl cellulose. Natural gums such as karaya, gum arabic, and gum tragacanth can also be incorporated. Colloidal magnesium aluminum silicate can also be used as component of the thickening composition to further improve the composition's texture. In certain embodiments, thickening agents in an amount of 0.5% to 5.0% by weight of the total composition are used.

The compositions may include an anionic polymer, for example in an amount of from 0.05 to 5%. Such agents are known generally for use in dentifrice, although not for this particular application, useful in composition are disclosed in U.S. Pat. Nos. 5,188,821 and 5,192,531; and include synthetic anionic polymeric polycarboxylates, such as 1:4 to 4:1 copolymers of maleic anhydride or acid with another polymerizable ethylenically unsaturated monomer, preferably methyl vinyl ether/maleic anhydride having a molecular weight (M.W.) of 30,000 to 1,000,000, most preferably 300,000 to 800,000. These copolymers are available for example as Gantrez. e.g., AN 139 (M.W. 500,000), AN 119 (M.W. 250,000) and preferably S-97 Pharmaceutical Grade (M.W. 700,000) available from ISP Technologies, Inc., Bound Brook, N.J. 08805. The enhancing agents when present are present in amounts ranging from 0.05 to 3% by weight. Other operative polymers include those such as the 1:1 copolymers of maleic anhydride with ethyl acrylate, hydroxyethyl methacrylate, N-vinyl-2-pyrollidone, or ethylene, the latter being available for example as Monsanto EMA No. 1103, M.W. 10,000 and EMA Grade 61, and 1:1 copolymers of acrylic acid with methyl or hydroxyethyl methacrylate, methyl or ethyl acrylate, isobutyl vinyl ether or N-vinyl-2-pyrrolidone. Suitable generally, are polymerized olefinically or ethylenically unsaturated carboxylic acids containing an activated carbon-to-carbon olefinic double bond and at least one carboxyl group, that is, an acid containing an olefinic double bond which readily functions in polymerization because of its presence in the monomer molecule either in the alpha-beta position with respect to a carboxyl group or as part of a terminal methylene grouping. Illustrative of such acids are acrylic, methacrylic, ethacrylic, alpha-chloroacrylic, crotonic, beta-acryloxy propionic, sorbic, alpha-chlorsorbic, cinnamic, beta-styrylacrylic, muconic, itaconic, citraconic, mesaconic, glutaconic, aconitic, alpha-phenylacrylic, 2-benzyl acrylic, 2-cyclohexylacrylic, angelic, umbellic, fumaric, maleic acids and anhydrides. Other different olefinic monomers copolymerizable with such carboxylic monomers include vinylacetate, vinyl chloride, dimethyl maleate and the like. Copolymers contain sufficient carboxylic salt groups for water-solubility. A further class of polymeric agents includes a composition containing homopolymers of substituted acrylamides and/or homopolymers of unsaturated sulfonic acids and salts thereof, in particular where polymers are based on unsaturated sulfonic acids selected from acrylamidoalykane sulfonic acids such as 2-acrylamide 2 methylpropane sulfonic acid having a molecular weight of 1,000 to 2,000,000, described in U.S. Pat. No. 4,842,847, Jun. 27, 1989 to Zahid. Another useful class of polymeric agents includes polyamino acids containing proportions of anionic surface-active amino acids such as aspartic acid, glutamic acid and phosphoserine, e.g. as disclosed in U.S. Pat. No. 4,866,161 Sikes et al.

Water:

The oral compositions may comprise significant levels of water. Water employed in the preparation of commercial oral compositions should be deionized and free of organic impurities. The amount of water in the compositions includes the free water which is added plus that amount which is introduced with other materials.

Humectants:

Within certain embodiments of the oral compositions, it is also desirable to incorporate a humectant to prevent the composition from hardening upon exposure to air. Certain humectants can also impart desirable sweetness or flavor to dentifrice compositions. Suitable humectants include edible polyhydric alcohols such as glycerine, sorbitol, propylene glycol as well as other polyols and mixtures of these humectants. In one embodiment, the principal humectant is glycerin, which may be present at levels of greater than 25%, e.g. 25-35% 30%, with 5% or less of other humectants.

Other Optional Ingredients:

In addition to the above-described components, the oral care embodiments can contain a variety of optional dentifrice ingredients some of which are described below. Optional ingredients include, for example, but are not limited to, adhesives, sudsing agents, flavoring agents, sweetening agents, additional antiplaque agents, abrasives, and coloring agents. These and other optional components are further described in U.S. Pat. No. 5,004,597, to Majeti; U.S. Pat. No. 3,959,458 to Agricola et al. and U.S. Pat. No. 3,937,807, to Haefele, all being incorporated herein by reference.

Unless stated otherwise, all percentages of composition components given in this specification are by weight based on a total composition or formulation weight of 100%.

The compositions and formulations as provided herein are described and claimed with reference to their ingredients, as is usual in the art. As would be evident to one skilled in the art, the ingredients may in some instances react with one another, so that the true composition of the final formulation may not correspond exactly to the ingredients listed. Thus, it should be understood that the composition extends to the product of the combination of the listed ingredients.

As used throughout, ranges are used as shorthand for describing each and every value that is within the range. Any value within the range can be selected as the terminus of the range. In addition, all references cited herein are hereby incorporated by referenced in their entireties. In the event of a conflict in a definition in the present disclosure and that of a cited reference, the present disclosure controls.

Unless otherwise specified, all percentages and amounts expressed herein and elsewhere in the specification should be understood to refer to percentages by weight. The amounts given are based on the active weight of the material.

EXAMPLE 1

Synthesis and Characterization of Zinc-Lysine Complex ZLC

The general reaction for formation of ZLC is as follows:

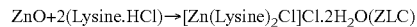

$$ZnO+2(Lysine.HCl) \rightarrow [Zn(Lysine)_2Cl]Cl.2H_2O(ZLC)$$

A 2:1 molar ratio of ZnO:Lysine.HCl suspension is prepared with stirring at room temperature for 12 hours. The mixture is centrifuged. 1 ml of supernatant is transferred into an NMR tube. The NMR tube is then placed in a closed test tube filled with ethanol for crystal growth. A number of colorless, cubic crystals are formed after a week. The crystal structure of ZLC crystal is determined by single crystal X-ray diffraction. ZLC has an empirical formula as $C_{12}H_{32}N_4O_6Cl_2Zn$ with molecular weight of 463 g/mol. The dimension of this complex molecule is 1.7 nm*7.8 nm*4.3 nm. In this complex, Zn cation is coordinated by two two lysine ligands with two N atoms from $NH_2$ groups and O atoms from carboxylic groups in an equatorial plane. It displays a distorted square-pyramidal geometry with the apical position occupied by a Cl atom. This novel structure gives rise to a positive cation moiety, to which a Cl anion is combined to form an ionic salt.

Laboratory Scale-Up Synthesis of Pure ZLC Powder:

2 mole of LysineHCl is dissolved in 1000 ml DI water with stirring at room temperature, 1 mole of solid ZnO is added slowly to the LysineHCl solution with stirring and the stirring is continued at RT overnight (12 hours). The suspension solution is centrifuged at high speed for 15 mins. The supernatant is slowly poured into EtOH. A precipitate is formed immediately. Approximately 5-8 ml EtOH is needed to get 1 g powder. The EtOH solvent with powder is filtered, and an off-white powder is obtained. The powder is placed in a 50° C. oven for drying and an 88% yield of product is obtained. PXRD confirms the purity of ZLC powder compared to ZLC crystal (FIG. 1 of PCT/US2012/70498).

EXAMPLE 2

Mechanisms of Sweat Reduction

Hydrolysis Reaction:

A 185 mg/ml ZLC solution is prepared and diluted several-fold and aged in a 37° C. oven over 5 hours for turbidity studies. A white precipitate forms as the solution is diluted. Turbidity of the solutions is measured using a nephelometer, results being given in nephelometric turbidity units (NTU). Table 1 shows a comparison of pH and turbidity before and after aging, showing an increase in turbidity with dilution and with aging:

TABLE 1

|  | 185 mg/ml | 92.5 mg/ml | 46.25 mg/ml | 23.125 mg/ml | 11.56 mg/ml | 5.78 mg/ml |
|---|---|---|---|---|---|---|
| initial pH | 6.8 | 7.0 | 7.4 | 7.7 | 7.8 | 8.0 |
| initial turbidity (NTU) | 4.75 | 2.78 | 1.48 | 0.70 | 14.8 | 40.1 |
| pH after aging | 6.8 | 7.0 | 7.4 | 7.7 | 7.8 | 8.0 |
| turbidity after aging (NTU) | 4.08 | 2.60 | 2.81 | 247.4 | >1000 | >1000 |

The precipitates formed in the 8×, 16× and 32× diluted solutions are collected by centrifugation and identified as crystalline ZnO by PXRD. From the supernatant, a single crystal is grown and shown by X-ray diffraction to be Lysine Monohydrochloride Dihydrate (Lysine.HCl.2H$_2$O). These data indicate that the ZLC complex disassociates upon dilution, with consequent precipitation of zinc oxide, while the lysine remains in solution.

The mechanism of the ZLC hydrolysis reaction can be expressed as

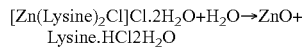

[Zn(Lysine)$_2$Cl]Cl.2H$_2$O+H$_2$O→ZnO+ Lysine.HCl2H$_2$O

In an underarm product, a mixture of ZnO+lysine HCl, in the presence of sweat, will form ZLC, which will enter the sweat duct and form a plug of ZnO.

Flocculation:

Another mechanism by which the ZLC blocks sweat release involves flocculation of ZLC in the presence of protein. Bovine Serum Albumin (BSA) is used as the protein in this study. Control solution (DI water) and three 1% BSA aqueous solutions with different pH are prepared as set forth on Table 2:

TABLE 2

|  | sample 1 | sample 2 | sample 3 |
|---|---|---|---|
| H$_2$O | 15 ml | 15 ml | 15 ml |
| BSA | 0 g | 155.1 mg | 155.2 mg |
| % BSA w/w | 0% | 1% | 1% |
| pH | 6.44 | 7.17 | adjusted to 5.13 |
| Turbidity(NTU) | 0.348 | 3.564 | 10.62 |
| Observation | Transparent | Transparent | Transparent |

ZLC powder is added to the above samples to study the interaction between ZLC and BSA and to determine whether ZLC has astringent properties, i.e., whether it can form a precipitate and thus behave as an antiperspirant. Turbidity and pH of solutions are measured 5 hours after the mixtures were placed in a 37° C. oven, and the results are shown in Table 3:

TABLE 3

|  | sample 1 | sample 2 | sample 3 |
|---|---|---|---|
| ZLC added | 151.1 mg | 151.1 mg | 150.9 mg |
| ZLC concentration in solution | 0.98% w/w or 15 mg/ml | 0.96% w/w or 15 mg/ml | 0.96% w/w or 15 mg/ml |
| observation | transparent solution becomes slightly cloudy | a lot white precipitate formed, solution becomes very cloudy | a lot white precipitate formed, solution becomes very cloudy |
| pH | 7.98 | 8.16 | 7.97 |
| Turbidity(NTU) | 357 | >1000 | >1000 |

Thus, in the sweat duct (pH=5-7), ZLC will hydrolyze to insoluble ZnO to physically block the sweat ducts. In addition, ZLC also has the ability to flocculate proteins in the sweat, similar to the flocculation of BSA above, thus enhancing the formation of "plugs" in the sweat ducts.

EXAMPLE 3

Antibacterial Effects

A zone of inhibition test is conducted on several materials: zinc oxide, lysine hydrochloride, and ZLC. The method involves making a lawn of freshly prepared bacterial culture on TSA (trypticase soy agar) plates. Sterile filter paper discs are seeded with 20 μl of test sample (supernatant or mixture). Sample-coated filter paper discs are air dried and applied onto the bacterial lawn on TSA plates. Plates are incubated for 20 hours at 37° C. ZLC has better antibacterial activity than zinc oxide alone or lysine hydrochloride alone.

EXAMPLE 4

Formulation Combining ZLC and Cysteine

It is found that cysteine together with ZLC solution is an improvement over a solution comprising ZLC alone, as it not only stabilizes ZLC solution at neutral pH, but also provides rapid precipitate with improved acid resistance. This composition is able to enhance sweat reduction and also boost insoluble zinc deposition when ZLC is used for personal care products as a visual indicator and antibacterial property, or in oral care products to deliver zinc to the tooth surface and to the microtubules. As seen in the above examples, the insoluble ZnO formed from the dilution of ZLC solution makes ZLC complex suitable for a next generation non-aluminum antiperspirant active. When used in underarm products, this ZLC complex will be diluted by sweat to form ZnO which can block sweat ducts, and therefore can prevent additional sweat from coming out of the skin. However, under the weak acidic environment of sweat (pH normally varied from 5 to 7), ZnO is gradually dissolved, which reduces efficacy as this degrades the plug formed at the sweat ducts.

A solution of ZLC solution at a concentration of 2.4% Zn by weight is prepared in accordance with Example 1. A ZLC/Cysteine solution is prepared by mixing 1.0019 g of cysteine solid (Sigma, M31952, FW 121.16 g/mol) with 200.26 g of the ZLC solution under stirring. After one hour, all cysteine is dissolved, the solution is transparent and the pH of the solution is 6.91. To 10 ml of this ZLC-Cys solution, 90 ml of DI water is added to prepare a total of 100 ml "stock" solution.

Turbidity study of diluted solutions: Turbidity measurements are conducted by Turbiscan (Formulaction Inc, Davie, Fla.). The measurement of this instrument is performed by sending out a light beam through the cell with sample solution and detecting the photons that cross the solution without being diffused. The result is shown in percent transmission—a higher percent transmission corresponds to a clearer solution, and a decrease of percent transmission indicates the formation of precipitate in solution. The temperature of the instrument is set at 37° C. Turbidity is measured in a one minute interval for 30 minutes under this temperature. All dilutions are freshly prepared before measurements.

Table 4 describes the details, the amount of stock solutions and water added, and the pH of dilutions. The pH rises upon dilution, because the dilution triggers precipitation of the zinc oxide complex, leaving the relatively basic lysine in solution.

TABLE 4 pH value of dilutions from "stock" solution

| | "stock" | 2 fold | 3 fold | 4 fold | 5 fold | 6 fold | 7 fold | 8 fold |
|---|---|---|---|---|---|---|---|---|
| "stock" solution(ml) | 24 | 12 | 8 | 6 | 4.8 | 4 | 3.4 | 3 |
| DI water(ml) | — | 12 | 16 | 18 | 19.2 | 20 | 20.4 | 21 |
| Total | 24 | 24 | 24 | 24 | 24 | 24 | 23.8 | 24 |
| pH | 7.60 | 7.90 | 7.86 | 7.95 | 7.94 | 7.98 | 8.04 | 8.03 |

The turbidity measurements are provided in Table 5 below. While the original "stock" solution remains transparent during the whole measurement period, the solutions which are further diluted all become visibly cloudy. A slow formation of precipitate is observed in 2 fold dilution, the rate of precipitate formation increases slightly after 15 minutes, and precipitate keeps forming in the 30 minute period. In 3 fold dilution, precipitate forms rapidly and does not stop during measurement period. Formation of precipitate in 4 fold dilution is found to be rapid initially, however, the rate of precipitation slows down after 20 minutes. Precipitate is formed immediately right after the "stock" solution is diluted in 5 fold, 6 fold, 7 fold and 8 fold dilutions. After 5 minutes, the precipitation process in all these dilutions slows down. Then, after 20 minutes, there is a slight increase of percent transmission in these dilutions, which suggest sedimentation occurs. Data from the plot also indicates that while the speed of precipitate formation increases as "stock" solution is more diluted, at higher dilutions, the total amount of precipitate formed seems to decrease, so that the maximum precipitation is observed at 3 fold dilution.

In order to study if the precipitate formed from this mixture could resist weak acidic pH, the pH of 2 fold dilution is adjusted to 5.5 (the average pH of human sweat) by diluted HCl aqueous. It is observed that the dilution at pH 5.5 becomes more cloudy than the one at pH 7.9, which suggests more precipitate is formed under such pH. The percent transmission of 2 fold dilution at pH 7.9 is 75%, and the percent transmission of this solution at pH 5.5 is 56% measured by Turbiscan. The decrease in percent transmission from this in vitro study strongly indicates that a weak acidic environment should tend to enhance precipitate formation.

X-ray photoelectron spectroscopy (XPS) analysis of the precipitate reveals it is composed primarily of a 1:2 Zn-cysteine complex with ZnO, and also contains a small $ZnCO_3$ impurity.

Four other ZLC-amino acid mixture solutions, including ZLC-Arginine, ZLC-Glycine, ZLC-Histidine, and ZLC-Proline, are also prepared in the same method as ZLC-Cys solution, and the same experiments are conducted to study if the same property as ZLC-Cysteine could be found in these solutions. As diluted, precipitate is found from 3 fold dilutions. However, the precipitate is not acid-stable. When the pH of 3 fold dilutions is adjusted to 5.5, precipitate in all these four mixture dissolves. The precipitates in these cases do not appear to comprise amino acids, but are simply zinc oxide.

Adding cysteine, but not the other amino acids tested, allows the ZLC solution to form a more acid resistant white precipitate. In addition, the experimental results show that the formation of precipitate from this novel mixture will be enhanced under average sweat pH (pH 5.5). This phenomenon makes this novel mixture material ideal for use in underarm products. The nearly neutral pH of the zinc mixture solution and its precipitation property by dilution also allows formulation in oral care products, where the precipitate is able to plug microtubules in the teeth, thereby reducing dental hypersensitivity as well as delivering the antibacterial and erosion-inhibitory zinc ion to the tooth surface.

TABLE 5

Results of turbidity measurements in one minute interval for 30 minutes

| min | "stock" solution T(t) 5 mm-45 mm (%) | 2 fold dilution T(t) 5 mm-45 mm (%) | 3 fold dilution T(t) 5 mm-45 mm (%) | 4 fold dilution T(t) 5 mm-45 mm (%) |
|---|---|---|---|---|
| 0 | 90.69 | 89.08 | 88.01 | 86.91 |
| 1 | 90.63 | 89.06 | 87.1 | 83.66 |
| 2 | 90.58 | 88.99 | 85.9 | 81.4 |
| 3 | 90.53 | 88.93 | 84.43 | 79.65 |
| 4 | 90.48 | 88.86 | 82.78 | 78.18 |
| 5 | 90.43 | 88.79 | 81.06 | 76.9 |
| 6 | 90.41 | 88.71 | 79.36 | 75.81 |
| 7 | 90.4 | 88.62 | 77.74 | 74.81 |
| 8 | 90.37 | 88.52 | 76.22 | 73.92 |
| 9 | 90.34 | 88.38 | 74.81 | 73.15 |
| 10 | 90.34 | 88.22 | 73.52 | 72.37 |
| 11 | 90.33 | 88.03 | 72.33 | 71.79 |
| 12 | 90.31 | 87.82 | 71.24 | 71.2 |
| 13 | 90.3 | 87.54 | 70.25 | 70.7 |
| 14 | 90.29 | 87.21 | 69.33 | 70.23 |
| 15 | 90.29 | 86.85 | 68.51 | 69.81 |

TABLE 5-continued

Results of turbidity measurements in one minute interval for 30 minutes

| | | | | |
|---|---|---|---|---|
| 16 | 90.28 | 86.44 | 67.74 | 69.42 |
| 17 | 90.27 | 85.97 | 67.03 | 69.09 |
| 18 | 90.28 | 85.46 | 66.37 | 68.78 |
| 19 | 90.27 | 84.9 | 65.76 | 68.5 |
| 20 | 90.26 | 84.32 | 65.19 | 68.27 |
| 21 | 90.26 | 83.69 | 64.66 | 68.06 |
| 22 | 90.25 | 83.06 | 64.16 | 67.85 |
| 23 | 90.24 | 82.4 | 63.69 | 67.68 |
| 24 | 90.23 | 81.74 | 63.26 | 67.58 |
| 25 | 90.23 | 81.08 | 62.86 | 67.5 |
| 26 | 90.23 | 80.43 | 62.5 | 67.45 |
| 27 | 90.22 | 79.77 | 62.19 | 67.44 |
| 28 | 90.22 | 79.11 | 61.9 | 67.39 |
| 29 | 90.21 | 78.48 | 61.64 | 67.48 |
| 30 | 90.2 | 77.9 | 61.24 | 67.54 |

| Min | 5 fold dilution T(t) 5 mm-45 mm (%) | 6 fold dilution T(t) 5 mm-45 mm (%) | 7 fold dilution T(t) 5 mm-45 mm (%) | 8 fold dilution T(t) 5 mm-45 mm (%) |
|---|---|---|---|---|
| 0 | 85.19 | 84.16 | 83.93 | 84.77 |
| 1 | 81.48 | 81.05 | 80.53 | 81.99 |
| 2 | 79.33 | 79.47 | 78.86 | 80.63 |
| 3 | 77.77 | 78.3 | 77.71 | 79.7 |
| 4 | 76.52 | 77.38 | 76.81 | 78.96 |
| 5 | 75.46 | 76.61 | 76.05 | 78.36 |
| 6 | 74.53 | 75.93 | 75.4 | 77.86 |
| 7 | 73.72 | 75.34 | 74.83 | 77.41 |
| 8 | 73 | 74.84 | 74.35 | 77.01 |
| 9 | 72.37 | 74.37 | 73.93 | 76.67 |
| 10 | 71.81 | 73.97 | 73.55 | 76.38 |
| 11 | 71.32 | 73.6 | 73.22 | 76.12 |
| 12 | 70.86 | 73.27 | 72.94 | 75.9 |
| 13 | 70.47 | 73 | 72.7 | 75.71 |
| 14 | 70.1 | 72.72 | 72.49 | 75.56 |
| 15 | 69.8 | 72.47 | 72.28 | 75.44 |
| 16 | 69.53 | 72.27 | 72.12 | 75.33 |
| 17 | 69.27 | 72.06 | 71.96 | 75.23 |
| 18 | 69.05 | 71.91 | 71.88 | 75.15 |
| 19 | 68.85 | 71.84 | 71.82 | 75.04 |
| 20 | 68.7 | 71.77 | 71.72 | 74.95 |
| 21 | 68.54 | 71.73 | 71.81 | 74.93 |
| 22 | 68.45 | 71.65 | 72.03 | 74.94 |
| 23 | 68.43 | 71.82 | 72.22 | 75.08 |
| 24 | 68.42 | 72.02 | 72.25 | 75.16 |
| 25 | 68.5 | 72.06 | 72.24 | 75.54 |
| 26 | 68.58 | 72.06 | 72.32 | 75.75 |
| 27 | 68.66 | 72.25 | 72.47 | 75.8 |
| 28 | 68.72 | 72.42 | 72.69 | 75.97 |
| 29 | 68.9 | 72.75 | 72.84 | 76.37 |
| 30 | 69.2 | 73.13 | 73.17 | 76.77 |

EXAMPLE 5

Liquid Hand Soap with ZLC 1 g of ZLC-Cys solution of Example 4 (prior to dilution to form the "stock" solution) is combined with 4 g of a commercial liquid hand soap (LHS) having a formulation as set forth in Table 6, to provide a formulation having 0.7% zinc.

TABLE 6

| Material | Weight % |
|---|---|
| Water and minors | Q.S. |
| Cetrimonium chloride (cetyl trimethyl ammonium chloride) | 2.4 |
| Glycerin | 2 |
| Lauramidopropyldimethylamine oxide | 1.2 |

TABLE 6-continued

| Material | Weight % |
|---|---|
| Cocamide MEA (cocomonoethanolamide) | 1 |
| PEG-120 methyl glucose dioleate | 0.6 |
| Myristamidopropylamine oxide | 0.4 |
| $C_{12-18}$ alkydimethylbenzyl ammonium chloride (BKC) | 0.13 |

The LHS/ZLC/cysteine solution at 0.7% zinc is then diluted 2 fold, 4 fold, 8 fold, 16 fold and 32 fold, and precipitation is measured. Optical Density (Absorbance) of LHS/ZLC/cysteine is obtained and compared with original LHS via Lambda 25 UV/VIS Spectrometer (PerkinElmer) at the wavelength of 610 nm. DI water sample are used as blank; the values shown in the table are compared to blank. Thus, a positive number means the sample is less transparent than the blank, and negative number indicates the sample being measured appears more transparent than the blank. As the original hand soap is diluted, it becomes more transparent. When the ZLC employed hand soap formula is diluted, the solution becomes cloudy, and the formation of a white precipitate is observed.

Comparing the dilution of original liquid hand soap and the ZLC/cysteine containing hand soap, the latter provides a significant signal for the phase change (from transparent to cloudy precipitation). Thus, ZLC can be incorporated into a commercial liquid hand soap and will act as a visual/sensory trigger during the washing process. In addition, the precipitate formed, ZnO/cysteine, enhances the antibacterial properties of the LHS, as well as providing a skin protection benefit.

EXAMPLE 6

Mouthwash Formulation

A mouthwash containing ZLC/Cysteine as active ingredient is formulated with the ingredients shown in Table 7.

TABLE 7

| Ingredients | % | Loading (g) |
|---|---|---|
| Sorbitol 70% sol | 5.50% | 27.5 |
| Aqueous ZLC solution 2.53%Zn plus 0.5% cysteine | 40.00% | 200 |
| Na Saccharin | 0.02% | 0.1 |
| Propylene Glycol | 7.00% | 35 |
| Poloxomer 407 | 0.40% | 2 |
| Citric Acid | 0.02% | 0.1 |
| Potassium Sorbitol | 0.05% | 0.25 |
| Glycerin | 7.50% | 37.5 |
| Peppermint Flavor | 0.10% | 0.5 |
| Deionized water | 39.4100% | 197.05 |
| Total | 100% | 500 |
| Zn % | 1% | |

The formulation can form a clear, stable solution but generates a precipitate when diluted. This mouthwash formulation has a neutral pH and is stable at 37° C. and on the shelf, but precipitates at dilute solution. This formation of insoluble precipitate by dilution allows formation of "plugs" in dentine tubules, providing benefits for hypersensitivity.

EXAMPLE 7

Gel Formulations Comprising Zinc-Lysine

The mouthwash formulation of the preceding example provides a clear formulation and precipitation when diluted by water. This unique property facilitates anti-sensitive and anti-cavity effects, and it is thus of interest in a toothpaste product.

An oral gel toothpaste with ZLC/cysteine as active ingredient is formulated. The precipitation property of ZLC gel phase is also investigated by hydrolysis reaction study, to determine whether when the teeth are being brushed with toothpaste containing ZLC/cysteine, the insoluble particles formed during brushing can penetrate into the dentin tubules and block the tubules resulting in an anti-sensitivity effect and signal for the consumer.

A gel with ZLC/cysteine as active ingredient is formulated with the ingredients shown in Table 5. The clarity and the precipitation by dilution is evaluated. Zinc ion concentration in the following batches is at 0.5% (w/w) zinc level.

TABLE 8

Oral gel with ZLC/cysteine

| Ingredients | % | Loading (g) |
|---|---|---|
| Sorbitol 70% sol | 76.03% | 380.15 |
| Aqueous ZLC solution 2.53%Zn plus 0.5% cysteine | 20.00% | 100 |
| Carboxymethyl cellulose (CMC) and Trimethyl cellulose (TMC) | 0.70% | 3.5 |
| Na Saccharin | 0.27% | 1.35 |
| Propylene Glycol | 3.00% | 15 |
| Total | 100.00% | 500 |
| % Zn | 0.506% | |
| Propylene Glycol | 3.00% | 15 |
| DI water | 15.07% | 75.35 |
| Total | 100.00% | 500 |

Lambda 25 UV/VIS Spectrometer (PerkinElmer) is used to obtain absorbance information in order to evaluate the clarity of gel phase. Absorbance is a logarithmic measure of the amount of light that is absorbed when passing through a substance. Since the particles in the gel absorb light, the more particles existing in solution, the more light absorbed by the gel. Thus, a small number of absorbance of a gel indicates a higher clarity. The absorbance is corrected by using deionized (DI) water as the blank solution under the light source wavelength of 610 nm.

Dilution Experiment:

The gel is diluted into 2 fold, 4 fold, 8 fold, 16 fold and 32 fold, and absorbance measured, with increased absorbance corresponding to precipitation.

The gel can be used alone or in a toothpaste having a gel phase and an abrasive paste phase. ZLC/cysteine as active ingredient in gel phase of toothpaste formulation. The formation of insoluble precipitate by dilution facilitates the formation of "plugs" in dentine tubules after using this type of toothpaste, and moreover, it provides a white precipitate signal during consumer use.

EXAMPLE 8

Plugging of Dentinal Tubules

Dentinal occlusion by an oral gel with ZLC/cysteine is measured compared to an oral gel without ZLC for potential anti-hypersensitivity benefit. A Flodec instrument is used to measure fluid flow through dentin tubules. A Pashley cell method (e.g., Pashley DH, O'Meara. J A, Kepler E E, et al. Dentin permeability effects of desensitizing dentifrices in vitro. *J Periodontol*. 1984; 55(9):522-525) is used following a procedure used to measure dentinal occlusion on mouth wash formulations by S. Mello. Two 10 minute treatments of 400 μl sample are applied with a pipette on dentin disks at 10 minute intervals. After each treatment the disks are rinsed with phosphate buffered saline (PBS) and measured for flow using a FLODEC apparatus, a device which tracks the position of a meniscus inside a capillary tithe to measure small changes in volume.

EXAMPLE 9

Visual Evaluation of Plugging Dentinal Tubules

The ZLC/cysteine is shown to be effective in occluding dentinal tubules when applied to the teeth and diluted to trigger precipitation. This deposition and tubule occlusion should reduce sensitivity and furthermore provides a reservoir of zinc to help protect the enamel against erosion and bacterial colonization.

Human dentin slices are prepared from whole human teeth. The teeth are cut into sections of ca. 800 microns. The sections are polished and any enamel on the section is ground off, so the sections appear as porous dentin material. The sections are then etched with 1% citric acid solution, rinsed, and stored in Phosphate Buffered Saline (PBS pH 7.4, Gibco Cat. No. 10010).

The thin slices of human dentin sections are imaged on the confocal microscope for baseline characterization. Top view images are taken in XYZ mode, and side view images were taken in XZY mode. Typical images are taken with a 50× objective lens, and with ×4 digital magnification. When a more global view is desired at lower magnification, the images are taken at ×1 digital magnification.

The thin slices of human dentin sections are treated using the respective treatment solutions. The treated thin slices are examined under the confocal microscope for signs of occlusion and deposition on the surface. Repeat treatments are made on the treated discs using the same or substantially same treatment procedure as the prior treatment. Confocal images are taken to monitor the progress of additional occlusion and deposition after one or more repeat treatments.

EXAMPLE 10

Dentifrice Formulation Comprising ZLC/Cysteine

Test dentifrice comprising ZLC/cysteine, 1450 ppm fluoride, and phosphates is prepared as follows:

| Ingredient | |
|---|---|
| PEG600 | 3.0 |
| CMC-7 | 0.65 |
| Xanthan | 0.2 |
| Sorbitol | 27.0 |
| Glycerin | 20.0 |
| Saccharin | 0.3 |
| Tetrasodium pyrophosphate | 0.5 |
| Calcium pyrophosphate | 0.25 |
| Sodium phosphate dibasic | 3.5 |
| Sodium fluoride (to provide 1450 ppm fluoride) | 0.32 |
| Water | QS |
| Titanium dioxide | 0.5 |

-continued

| Ingredient | |
|---|---|
| Abrasive silica | 8.0 |
| Thickener silica | 8.0 |
| Aqueous ZLC solution 2.53%Zn plus 0.5% cysteine | 20 |
| Sodium lauryl sulfate | 1.5 |
| Flavoring | 1.2 |

The invention claimed is:

1. A composition comprising (i) a zinc (amino acid or trialkyl glycine) halide complex and (ii) cysteine in free or in orally or cosmetically acceptable salt form.

2. The composition according to claim 1, wherein the zinc (amino acid or tralkyl glycine) halide is formed from precursors, wherein the precursors are a zinc ion source, an amino acid source, and a halide source, wherein the halide source can be part of the zinc ion source, the amino acid source, or a halogen acid.

3. The composition according to claim 2, wherein the zinc ion source is at least one of zinc oxide, zinc chloride, zinc carbonate, zinc nitrate, zinc citrate, and zinc phosphate.

4. The composition according to claim 2, wherein the amino acid source is at least one of a basic amino acid, lysine, arginine, and glycine.

5. The composition according to claim 1, wherein the trialkyl glycine is a $C_1$-$C_4$ alkyl glycine or trimethyl glycine.

6. The composition according to claim 1 wherein the zinc amino acid halide is made by combining zinc oxide with an amino acid hydrohalide.

7. The composition according to claim 1 wherein the zinc amino acid halide has the formula $Zn(Amino\ Acid)_2Hal_2$ or $Zn(Amino\ Acid)_3Hal_2$, wherein Zn is a divalent zinc ion and Hal is a halide ion.

8. The composition according to claim 1 wherein the zinc amino acid halide complex is $[Zn(C_6H_{14}N_2O_2)_2Cl]^+Cl^-$.

9. The composition according to claim 1 which upon dilution with water, provides a precipitate comprising zinc oxide in complex with cysteine, and optionally additionally comprising zinc oxide, zinc carbonate, and mixtures thereof.

10. The composition according to claim 1 wherein the total amount of zinc present in the composition is 0.2 to 8% by weight of the composition.

11. The composition according to claim 1, wherein the cysteine is cysteine hydrohalide, optionally cysteine hydrochloride.

12. The composition according to claim 1 which is an antiperspirant or deodorant product, further comprising a cosmetically acceptable carrier.

13. A method of killing bacteria, reducing perspiration, and/or reducing body odor comprising applying to skin an effective amount of the composition of claim 12.

14. The composition of claim 1 which is a personal care product selected from liquid hand soap, body wash, dermal lotions, dermal creams, and dermal conditioners further comprising a cosmetically acceptable carrier.

15. A method of killing bacteria, treating or reducing the incidence of acne or topical skin infections, or to provide a visual signal when washing, comprising washing the skin with water and an effective amount of the composition of claim 14.

16. The composition of claim 1 which is an oral care product, further comprising an orally acceptable carrier.

17. A method to reduce and inhibit acid erosion of the enamel, clean the teeth, reduce bacterially-generated biofilm and plaque, reduce gingivitis, inhibit tooth decay and formation of cavities, and/or reduce dentinal hypersensitivity comprising applying an effective amount of a composition according to claim 16 to the oral cavity of a person in need thereof.

* * * * *